(12) United States Patent
Hanbury

(10) Patent No.: US 12,691,247 B2
(45) Date of Patent: Jul. 28, 2026

(54) SYSTEMS AND METHODS FOR VISUAL CORTEX TARGETING AND TREATMENT

(71) Applicant: Sana Health, Inc., Lafayette, CO (US)

(72) Inventor: Richard Hanbury, Lafayette, CO (US)

(73) Assignee: SANA HEALTH INC., Louisville, CO (US)

( * ) Notice: Subject to any disclaimer, the term of this patent is extended or adjusted under 35 U.S.C. 154(b) by 1041 days.

(21) Appl. No.: 17/726,989

(22) Filed: Apr. 22, 2022

(65) Prior Publication Data

US 2022/0249803 A1 Aug. 11, 2022

Related U.S. Application Data

(63) Continuation-in-part of application No. 17/005,047, filed on Aug. 27, 2020, now Pat. No. 11,679,231, (Continued)

(51) Int. Cl.

*A61M 21/02* (2006.01)
*A61M 21/00* (2006.01)

(52) U.S. Cl.

CPC ..... *A61M 21/02* (2013.01); *A61M 2021/0022* (2013.01); *A61M 2021/0027* (2013.01); (Continued)

(58) Field of Classification Search

CPC .................. A61M 21/00; A61M 21/02; A61M 2021/0005; A61M 2021/0011; (Continued)

(56) References Cited

U.S. PATENT DOCUMENTS 4,172,406 A 10/1979 Martinez
4,315,502 A 2/1982 Gorges
(Continued)

FOREIGN PATENT DOCUMENTS

AU 2016359154 A1 7/2018
CN 205814527 U 12/2016
(Continued)

OTHER PUBLICATIONS

Aimee Corso, "Cognito Therapeutics Launched with Exclusive License to Promising Alzheimer's Research from the Massachusetts Institute of Technology", Business Wire, Boston and San Francisco, https://www.businesswire.com/news/home/20161207006042/en/Cognito-Therapeutics-Launched-Exclusive-License-Promising-Alzheimer%E2%80%99s, Dec. 7, 2016 (Dec. 7, 2016), 3 Pages.
(Continued)

*Primary Examiner* — Carrie R Dorna
(74) *Attorney, Agent, or Firm* — Dickinson Wright PLLC; Alex A. Courtade; Kristopher Lance Anderson

(57) ABSTRACT

Disclosed are systems and methods for a computerized framework that detects medical conditions within patients and dynamically effectuates a treatment. The disclosed framework is configured for controlling computerized medical equipment by analyzing data associated with a patient, determining underlying conditions of the patient, then automatically causing such equipment to output electronic stimuli that can address the medical condition(s) detected. The framework can determine a correlation between a patient's attributes, electronic data of a condition of a patient and a medical disorder, and cause a medical device to treat and monitor improvements of the condition and disorder. The framework can be configured to focus in on particular body parts of a patient that have been identified as a body part that enables treatment as well as a part that facilitates the most efficient treatment for a recovery.

20 Claims, 12 Drawing Sheets

Related U.S. Application Data which is a continuation of application No. 16/422,592, filed on May 24, 2019, now Pat. No. 11,141,559, which is a continuation of application No. 15/360,808, filed on Nov. 23, 2016, now Pat. No. 10,328,236.

(60) Provisional application No. 62/258,965, filed on Nov. 23, 2015.

(52) U.S. Cl.
CPC ................. *A61M 2021/005* (2013.01); *A61M 2205/3569* (2013.01); *A61M 2205/3592* (2013.01); *A61M 2205/505* (2013.01); *A61M 2209/088* (2013.01)

(58) Field of Classification Search
CPC .... A61M 2021/0044; A61M 2021/005; A61N 5/0613; A61N 5/0618; A61N 5/0622; A61N 2005/0626; A61N 2005/0629; A61N 2005/0635; A61N 2005/0643; A61N 2005/0645; A61N 2005/0647; A61N 2005/0648
See application file for complete search history.

(56) References Cited

U.S. PATENT DOCUMENTS

| | | | |
|---|---|---|---|
| 4,892,106 | A | 1/1990 | Gleeson |
| 4,966,164 | A | 10/1990 | Colsen et al. |
| 5,343,261 | A | 8/1994 | Wilson |
| 5,783,909 | A | 7/1998 | Hochstein |
| 6,123,661 | A | 9/2000 | Fukushima et al. |
| 6,409,655 | B1 | 6/2002 | Wilson et al. |
| 8,562,659 | B2 | 10/2013 | Wells et al. |
| 8,838,247 | B2 | 9/2014 | Hagedorn et al. |
| 8,852,073 | B2 | 10/2014 | Genereux et al. |
| 8,932,199 | B2 | 1/2015 | Berka et al. |
| D775,260 | S | 12/2016 | Gordon et al. |
| 9,649,469 | B2 | 5/2017 | Hyde et al. |
| D805,515 | S | 12/2017 | Bowes et al. |
| D827,701 | S | 9/2018 | Nguyen et al. |
| 10,328,236 | B2 | 6/2019 | Hanbury |
| 10,383,769 | B1 | 8/2019 | Miller |
| 10,449,326 | B2 | 10/2019 | Genereux et al. |
| 11,141,559 | B2 | 10/2021 | Hanbury |
| 2002/0198577 | A1 | 12/2002 | Jaillet |
| 2006/0106276 | A1 | 5/2006 | Shealy et al. |
| 2006/0252979 | A1 | 11/2006 | Vesely et al. |
| 2008/0269629 | A1 | 10/2008 | Reiner |
| 2009/0156886 | A1* | 6/2009 | Burgio ................ A61B 5/6805 607/45 |
| 2010/0056854 | A1 | 3/2010 | Chang |
| 2010/0161010 | A1 | 6/2010 | Thomas |
| 2010/0323335 | A1 | 12/2010 | Lee |
| 2011/0075853 | A1 | 3/2011 | Anderson |
| 2011/0213664 | A1 | 9/2011 | Osterhout et al. |
| 2011/0257712 | A1 | 10/2011 | Wells et al. |
| 2012/0095534 | A1 | 4/2012 | Schlangen et al. |
| 2012/0211013 | A1 | 8/2012 | Otis |
| 2013/0035734 | A1 | 2/2013 | Soler Fernandez et al. |
| 2013/0225915 | A1 | 8/2013 | Redfield et al. |
| 2013/0267759 | A1 | 10/2013 | Jin |
| 2013/0303837 | A1 | 11/2013 | Berka et al. |
| 2014/0336473 | A1 | 11/2014 | Greco |
| 2015/0231395 | A1 | 8/2015 | Saab |
| 2015/0268673 | A1 | 9/2015 | Farzbod et al. |
| 2016/0228771 | A1 | 8/2016 | Watson |
| 2017/0143935 | A1 | 5/2017 | Hanbury |
| 2017/0189639 | A1 | 7/2017 | Mastrianni |
| 2017/0252532 | A1 | 9/2017 | Holsti et al. |
| 2017/0312476 | A1 | 11/2017 | Woo |
| 2018/0184969 | A1 | 7/2018 | Zhao et al. |
| 2018/0250494 | A1 | 9/2018 | Hanbury |
| 2019/0030279 | A1 | 1/2019 | Nowlin |
| 2019/0262576 | A1 | 8/2019 | Mastrianni |
| 2019/0321584 | A1 | 10/2019 | Hanbury |
| 2019/0388020 | A1 | 12/2019 | Stauch et al. |
| 2020/0139112 | A1 | 5/2020 | Aharonovitch |
| 2020/0268341 | A1 | 8/2020 | Stroman |
| 2020/0368491 | A1 | 11/2020 | Poltorak |
| 2020/0390999 | A1 | 12/2020 | Hanbury |
| 2020/0391000 | A1 | 12/2020 | Hanbury |
| 2021/0008332 | A1 | 1/2021 | Jin et al. |
| 2022/0249803 | A1 | 8/2022 | Hanbury |
| 2022/0265959 | A1 | 8/2022 | Hanbury |
| 2022/0409849 | A1 | 12/2022 | Hanbury |

FOREIGN PATENT DOCUMENTS

| | | | |
|---|---|---|---|
| CN | 104546285 | B | 3/2017 |
| CN | 109152524 | A | 1/2019 |
| EA | 035285 | B1 | 5/2020 |
| WO | 2001064005 | A2 | 9/2001 |
| WO | 2012117343 | A1 | 9/2012 |
| WO | 2015028480 | A1 | 3/2015 |
| WO | 2016140408 | A1 | 9/2016 |
| WO | 2017091758 | A1 | 6/2017 |
| WO | 2018160903 | A1 | 9/2018 |
| WO | 2019060598 | A1 | 3/2019 |
| WO | 2019226656 | A1 | 11/2019 |
| WO | 2020172448 | A1 | 8/2020 |
| WO | 2020219350 | A1 | 10/2020 |
| WO | 2021007444 | A1 | 1/2021 |
| WO | 2021236421 | A1 | 11/2021 |

OTHER PUBLICATIONS

Angus Chen, "An Hour of Light and Sound a Day Might Keep Alzheimer's at Bay", Scientific American, https://www.scientificamerican.com/article/an-hour-of-light-and-sound-a-day-might-keep-alzheimers-at-bay/, Mar. 14, 2019 (Mar. 14, 2019), 5 Pages.

Anne Trafton, "Ed Boyden receives 2018 Canada Gairdner International Award", McGovern Institute, https://mcgovern.mit.edu/2018/03/27/ed-boyden-receives-2018-canada-gardner-international-award/, Mar. 27, 2018 (Mar. 27, 2018), 3 Pages.

Anthony J. Martorell, et al., "Multi-sensory Gamma Stimulation Ameliorates Alzheimer's-Associated Pathology and Improves Cognition", Cell, https://www.cell.com/cell/fulltext/S0092-8674(19)30163-1, Mar. 14, 2019 (Mar. 14, 2019). 16 Pages.

Chinnakkaruppan Adaikkan, et al., "Gamma Entrainment Binds Higher-Order Brain Regions and Offers Neuroprotection", Neuron, https://linkinghub.elsevier.com/retrieve/pii/S0896627319303460, May 7, 2019 (May 7, 2019), 18 Pages.

Damian Garde, "'Beyond amyloid': A look at what's next in Alzheimer's research", STAT, https://www.statnews.com/2017/08/18/beyond-amyloid-alzheimers-research/, Aug. 18, 2017 (Aug. 18, 2017), 5 Pages.

Dreamlight Zen; https://dreamlight.tech/products/dreamlight-zen; product description downloaded Aug. 3, 2021; 16 pages; Copyright 2021 Dreamlight.

Ed Yong, "Beating Alzheimer's With Brain Waves", The Atlantic, https://www.theatlantic.com/science/archive/2016/12/beating-alzheimers-with-brain-waves/509846/, Dec. 7, 2016 (Dec. 7, 2016), 8 Pages.

Hannah Devlin, "Strobe lighting provides a flicker of hope in the fight against Alzheimer's", The Guardian, https://www.theguardian.com/science/2016/dec/07/strobe-lighting-provides-a-flicker-of-hope-in-the-fight-against-alzheimers, Dec. 7, 2016 (Dec. 7, 2016), 3 Pages.

Hannah F. Iaccarino, et al., "Gamma frequency entrainment attenuates amyloid load and modifies microglia", Nature, Journal, vol. 540, Dec. 7, 2016 (Dec. 7, 2016), pp. 230-235.

Helen Thomson, "How flashing lights and pink noise might banish Alzheimer's, improve memory and more", Nature, https://www.nature.com/articles/d41586-018-02391-6, Feb. 28, 2018 (Feb. 28, 2018), 10 Pages.

(56) References Cited

OTHER PUBLICATIONS

Illumy by Sound Oasis; https://www.soundoasis.com/products/light-therapy/illumy-the-smart-sleep-mask/; Product description downloaded Aug. 2, 2021; 6 pages Copyright 2000-2021 AvivaHealth.com.
Jamie Ducharme, "The End of Alzheimer's?", Boston, Magazine, https://www.bostonmagazine.com/health/2017/11/27/li-huei-tsai-alzheimers-treatment/, Nov. 27, 2017 (Nov. 27, 2017), 4 Pages.
Liviu Aron, et al., "Neural synchronization in Alzheimer's disease", Nature, Journal, vol. 540, Dec. 7, 2016 (Dec. 7, 2016), pp. 207-208.
Lumos Smart Sleep Mask; https://lumos.tech/lumos-smart-sleep-mask/; Product description downloaded Aug. 3, 2021; 3 pages.
Meg Tirrell, "Could flashing light treat Alzheimer's? Fresh approaches to treating the disease", CNBC, https://www.cnbc.com/2017/03/29/could-flashing-light-treat-alzheimers-fresh-approaches-to-treating-the-disease.html, Mar. 29, 2017 (Mar. 29, 2017), 6 Pages.
Melissa Healy, "Flickering lights may illuminate a path to Alzheimer's treatment", Los Angeles Times, Dec. 7, 2016 (Dec. 7, 2016), 3 Pages.
Molly Webster, et al., "Bringing Gamma Back", WNYC Studios, https://www.wnycstudios.org/story/bringing-gammaback, Dec. 8, 2016 (Dec. 8, 2016), 3 Pages.
Nathan Hurst, "Could Flickering Lights Help Treat Alzheimer's?", Smithsonian, https://www.smithsonianmag.com/innovation/could-flickering-lights-help-treat-alzheimers-180961762/, Jan. 11, 2017 (Jan. 11, 2017), 2 Pages.
Nicole Wetsman, "Flickering light seems to help mice with Alzheimer's-like symptoms", Popular Science, https://www.popsci.com/flickering-light-genes-alzheimers, May 7, 2019 (May 7, 2019), 2 Pages.
NSTC, "First Friday Biosciences: Nov. 3 in Woburn", https://www.nstc.org/previous-events/first-friday-biosciencesnov-3-in-woburn/, Nov. 3, 2017 (Nov. 3, 2017), 8 Pages.
Pam Belluck, "A Possible Alzheimer's Treatment With Clicks and Flashes? It Worked on Mice", New York Times, https://www.nytimes.com/2019/03/14/health/alzheimers-memory.html, Mar. 14, 2019 (Mar. 14, 2019), 5 Pages.
Pam Belluck, "Could simply listening to this sound help cure Alzheimer's disease? MIT researchers are Investigating", Boston Globe, https://www.bostonglobe.com/news/science/2019/03/14/could-simply-listening-thissound-help-cure-alzheimer-disease-mit-researchers-are-investigating/2npZrAp8g9KLSfURbTxaVO/story.html, Mar. 14, 2019 (Mar. 14, 2019), 4 Pages.
Remee Lucid Dreaming Mask; http://sleepwithremee.com/; Product description downloaded Aug. 3, 2021; 10 pages; Copyright 2018 Bitbanger LLC.
Robert Weisman, "MIT team uses LEDs to attack Alzheimer's", Boston Globe, https://www.bostonglobe.com/business/2016/12/07/led-technology-from-mit-used-startup-working-alzheimer-treatment/Kbdjp9WvfoPLfC1bNhvGOI/story.html, Dec. 7, 2016 (Dec. 7, 2016), 4 Pages.
The Picower Institute, "Tsai earns Hans Wigzell Research Foundation Science Prize", https://picower.mit.edu/news/tsai-earns-hans-wigzell-research-foundation-science-prize, Jan. 23, 2019 (Jan. 23, 2019), 3 Pages.
European Patent Office, Extended European Search Report dated Nov. 27, 2020 for European Patent Application No. 18761087.8, 9 pages.
European Patent Office, Supplementary European Search Report mailed Jun. 5, 2019 for European Patent Application No. 16869299.4, 8 pages.
Intellectual Property India, Examination Report for Application No. 201837022885, dated May 6, 2021; 7 pages.
International Searching Authority, International Search Report and Written Opinion for PCT/US2016/063651, mailed Feb. 3, 2017; 13 pages.
International Searching Authority, International Search Report and Written Opinion for PCT/US2019/033322, mailed Aug. 2, 2019; 11 pages.
International Searching Authority, International Search Report and Written Opinion for PCT/US2020/019091, mailed May 6, 2020; 13 pages.
International Searching Authority, International Search Report and Written Opinion for PCT/US2020/41423, mailed Oct. 9, 2020; 9 pages.
International Searching Authority, International Search Report and Written Opinion for PCT/US2021/032260, mailed Aug. 31, 2021; 9 pages.
International Searching Authority, International Search Report and Written Opinion for PCT/US2018/020547, mailed May 7, 2018; 10 pages.
Canadian Intellectual Property Office, Office Action mailed Dec. 7, 2022 for Canadian Patent Application No. 3029198, 4 pages.

* cited by examiner

SYSTEMS AND METHODS FOR VISUAL CORTEX TARGETING AND TREATMENT

CROSS-REFERENCE TO RELATED APPLICATIONS

This patent application is a continuation-in-part (CIP) of and claims priority to U.S. application Ser. No. 17/005,047, filed Aug. 27, 2020 titled "Methods and systems for providing stimuli to the brain" (now published as U.S. Patent Application Publication No. 2020/0391000), which is a continuation of U.S. application Ser. No. 16/422,592 filed May 24, 2019, titled "Methods and systems for providing stimuli to the brain" (now published as U.S. Patent Application Publication No. 2019/0321584), which is a continuation of U.S. application Ser. No. 15/360,808 filed Nov. 23, 2016, titled "Methods and Systems for Providing Stimuli to the Brain" (now U.S. Pat. No. 10,328,236). As a continuation of U.S. application Ser. No. 17/005,047 and Ser. No. 16/422,592 and thus U.S. application Ser. No. 15/360,808, this application claims priority to U.S. Provisional Application No. 62/258,965, filed Nov. 23, 2015, and titled "Methods and Systems for Providing Audio and Visual Stimulus to Treat Neurological Disorders." All four applications are incorporated by reference herein in their entirety as if reproduced in full below.

FIELD OF THE DISCLOSURE

The present disclosure relates to medical devices and methods. In particular, the present disclosure relates to providing stimuli to a subject to treat various neurological disorders or conditions and/or to provide performance enhancement.

BACKGROUND

Sensory stimulation has been applied to treat various disorders. For example, binaural beats have applied to induce various mental states to encourage sleep, relaxation, meditation, creativity, and other desirable mental states. Combinations of auditory and visual stimuli have been applied to encourage such mental states as well. The application of such therapy, however, has been less than ideal in many circumstances. Equipment to provide the stimulus can be bulky, expensive, generally inaccessible, and below the critical efficacy threshold for widespread use, typically only helping subsets of the population. Users may find the use of such equipment difficult in many circumstances, such as when trying to sleep in a bedroom or an airplane cabin.

To treat various neurological disorders and conditions, pharmaceuticals and/or supplements are often used instead of sensory stimulation. The use of pharmaceuticals, however, can be less than ideal in many circumstances. Often, pharmaceuticals are expensive, rely on patient-compliance, and may require a prescription from a medical professional. Pharmaceuticals may be effective in only a small, less than ideal portion of the general population. To treat insomnia, for example, pharmaceuticals and supplements such as melatonin and zolpidem (e.g., AMBIEN™) have questionable efficacy. Pharmaceuticals often lead to undesirable side effects. For example, some pharmaceutical for treating insomnia can lead to deprivation in certain ranges of deep sleep and increases in mortality rates.

For at least these reasons, improved methods and systems to treat neurological disorders and other conditions that overcome at least some of the aforementioned challenges are desired.

SUMMARY

The present disclosure relates to medical devices and methods which may be used, for example, to provide stimulus to a subject to treat various neurological disorders or conditions, where the stimulus provided may include one or more of an auditory, a visual, or a tactile stimulus. Examples of neurological disorders which may be treated with devices and methods may include, but are not limited to, insomnia, post-traumatic stress disorder (PTSD), brain injuries including, but not limited to traumatic brain injury (TBI), mild traumatic brain injury (mTBI), or injury from oxygen deprivation of the brain from strokes, depression, anxiety, mood disorders, personality disorders, eating disorders, psychotic disorders, and balance disorders, to name a few. Alternatively or in combination, the stimulus provided by the medical devices and methods described herein may provide cognitive benefits and/or enhancement, including, but not limited to, improving neuroplasticity, motor skills, coordination, reaction times, alertness, energy, working memory, mood, and feelings of wellbeing.

In one aspect, a method of providing sensory stimulation to a user is disclosed. The method includes alternating sensory stimulation between a first sensory stimulation including simultaneously providing a left visual stimulus pattern to a left eye of the user and a right auditory stimulus pattern to the right side of a head of the user and a second sensory stimulation including simultaneously providing a right visual stimulus pattern to a right eye of the user and a left auditory stimulus pattern to the left side of the head. The first sensory stimulation and the second sensory stimulation each include a first stimulus pattern having a first pulse frequency, a second stimulus pattern having a second pulse frequency less than the first pulse frequency, and a third stimulus pattern having a third pulse frequency less than the second pulse frequency. One of the first pulse frequency, the second pulse frequency, or the third pulse frequency is between approximately 3.75 Hz and 4.25 Hz.

In another aspect, an apparatus to provide stimulation to a user is disclosed. The apparatus includes a frame configured to be worn on a head of the user and a controller programmed to generate a plurality of inputs including a left light source input, a right light source input, a left auditory source input, and a right auditory source input. The apparatus further includes a left light source configured to generate a left visual stimulus pattern from the left light source input and a right light source configured to generate a right visual stimulus pattern from the right light source input. The apparatus further includes a left auditory source configured to generate a left auditory stimulus pattern from the left auditory source input and a right auditory source configured to generate a right auditory stimulus pattern from the right auditory source input. The controller is programmed to generate inputs which alternate between a first input including simultaneously generating the left light source input and the right auditory source input and a second input including simultaneously generating the right light source input and the left auditory source input. The first input and the second input each include a first stimulus pattern having a first pulse frequency, a second stimulus pattern having a second pulse frequency less than the first pulse frequency, and a third stimulus pattern having a third pulse frequency less than the second pulse frequency. One of the first pulse frequency, the second pulse frequency, or the third pulse frequency is between 3.75 Hz and 4.25 Hz.

In yet another aspect, a method of treating a neurological disease or condition or providing performance enhancement is disclosed. The method includes providing a headset to be worn by a user and providing sensory stimulation to the user from the headset. The sensory stimulation alternates between a first sensory stimulation including simultaneously providing a left visual stimulus pattern to a left eye of the user and a right auditory stimulus pattern to the right side of a head of the user and a second sensory stimulation including simultaneously providing a right visual stimulus pattern to a right eye of the user and a left auditory stimulus pattern to the left side of the head. The first sensory stimulation and the second sensory stimulation each include a first stimulus pattern having a first pulse frequency, a second stimulus pattern having a second pulse frequency less than the first pulse frequency, and a third stimulus pattern having a third pulse frequency less than the second pulse frequency. One of the first pulse frequency, the second pulse frequency, or the third pulse frequency is between 3.75 Hz and 4.25 Hz.

These features together with the various ancillary provisions and features which will become apparent to those skilled in the art from the following detailed description, are attained by the methods and system for providing stimulation to a user of the present disclosure, embodiments thereof being shown with reference to the accompanying drawings, by way of example only, wherein:

BRIEF DESCRIPTION OF THE DRAWINGS

The features, and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure.

DETAILED DESCRIPTION OF EXAMPLE EMBODIMENTS

Figure 1A:
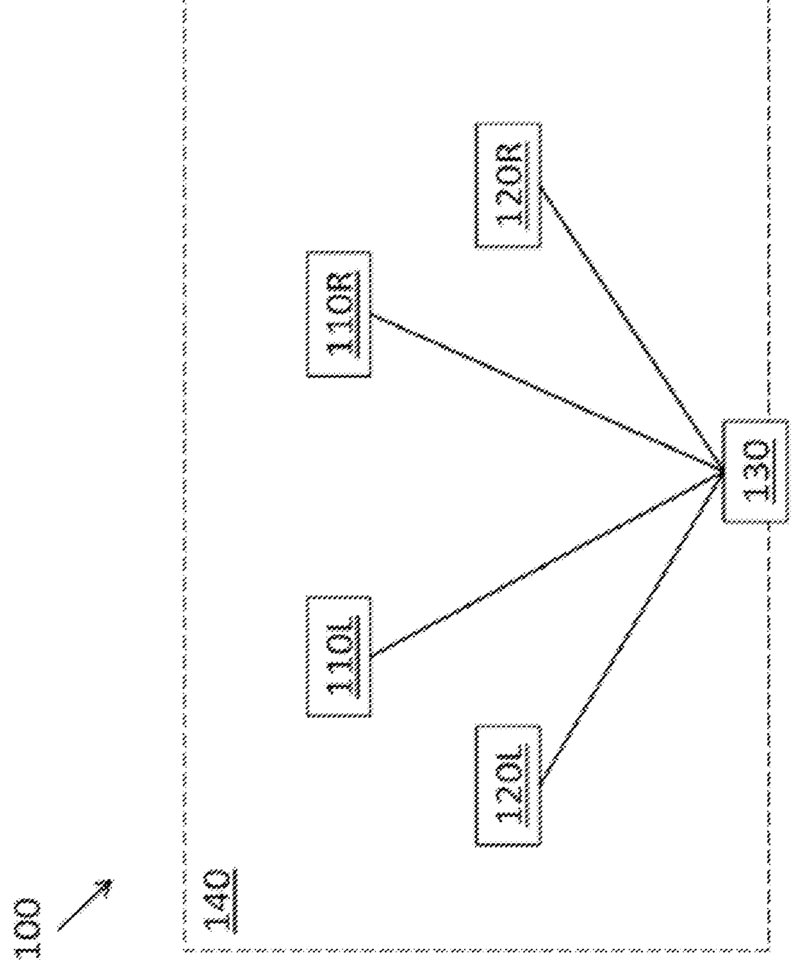
FIGS. 1A and 1B show schematic diagrams of therapeutic systems to provide therapeutic auditory, visual, and/or tactile stimulus according to some embodiments of the present disclosure.

The present disclosure will now be described more fully hereinafter with reference to the accompanying drawings, which form a part hereof, and which show, by way of non-limiting illustration, certain example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

Unless limited otherwise, the terms "connected," "coupled," and "mounted," and variations thereof herein are used broadly and encompass direct and indirect connections, couplings, and mountings. In addition, the terms "connected" and "coupled"" and variations thereof are not restricted to physical or mechanical connections or couplings. Further, terms such as "up," "down," "bottom," "top," "front," "rear," "upper," "lower," "upwardly," "downwardly," and other orientational descriptors are intended to facilitate the description of the exemplary embodiments of the present disclosure, and are not intended to limit the structure of the exemplary embodiments of the present disclosure to any particular position or orientation. Terms of degree, such as "substantially" or "approximately," are understood by those skilled in the art to refer to reasonable ranges around and including the given value and ranges outside the given value, for example, general tolerances associated with manufacturing, assembly, and use of the embodiments. The term "substantially," when referring to a structure or characteristic, includes the characteristic that is mostly or entirely present in the characteristic or structure.

The present disclosure is described below with reference to block diagrams and operational illustrations of methods and devices. It is understood that each block of the block diagrams or operational illustrations, and combinations of blocks in the block diagrams or operational illustrations, can be implemented by means of analog or digital hardware and computer program instructions. These computer program instructions can be provided to a processor of a general purpose computer to alter its function as detailed herein, a special purpose computer, ASIC, or other programmable data processing apparatus, such that the instructions, which execute via the processor of the computer or other programmable data processing apparatus, implement the functions/acts specified in the block diagrams or operational block or blocks. In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

For the purposes of this disclosure a non-transitory computer readable medium (or computer-readable storage medium/media) stores computer data, which data can include computer program code (or computer-executable instructions) that is executable by a computer, in machine readable form. By way of example, and not limitation, a computer readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, optical storage, cloud storage, magnetic storage devices, or any other physical or material medium which can be used to tangibly store the desired information or data or instructions and which can be accessed by a computer or processor.

For the purposes of this disclosure the term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Cloud servers are examples.

For the purposes of this disclosure a "network" should be understood to refer to a network that may couple devices so that communications may be exchanged, such as between a server and a client device or other types of devices, including between wireless devices coupled via a wireless network, for example. A network may also include mass storage, such as network attached storage (NAS), a storage area network (SAN), a content delivery network (CDN) or other forms of computer or machine readable media, for example. A network may include the Internet, one or more local area networks (LANs), one or more wide area networks (WANs), wire-line type connections, wireless type connections, cellular or any combination thereof. Likewise, sub-networks, which may employ differing architectures or may be compliant or compatible with differing protocols, may interoperate within a larger network.

For purposes of this disclosure, a "wireless network" should be understood to couple client devices with a network. A wireless network may employ stand-alone ad-hoc networks, mesh networks, Wireless LAN (WLAN) networks, cellular networks, or the like. A wireless network may further employ a plurality of network access technologies, including Wi-Fi, Long Term Evolution (LTE), WLAN, Wireless Router (WR) mesh, or 2nd, 3rd, $4^{th}$ or $5^{th}$ generation (2G, 3G, 4G or 5G) cellular technology, mobile edge computing (MEC), Bluetooth, 802.11b/g/n, or the like. Network access technologies may enable wide area coverage for devices, such as client devices with varying degrees of mobility, for example.

In short, a wireless network may include virtually any type of wireless communication mechanism by which signals may be communicated between devices, such as a client device or a computing device, between or within a network, or the like.

A computing device may be capable of sending or receiving signals, such as via a wired or wireless network, or may be capable of processing or storing signals, such as in memory as physical memory states, and may, therefore, operate as a server. Thus, devices capable of operating as a server may include, as examples, dedicated rack-mounted servers, desktop computers, laptop computers, set top boxes, integrated devices combining various features, such as two or more features of the foregoing devices, or the like.

For purposes of this disclosure, a client (or patient or user) device, referred to as user equipment (UE)), may include a computing device capable of sending or receiving signals, such as via a wired or a wireless network. A client device may, for example, include a desktop computer or a portable device, such as a cellular telephone, a smart phone, a display pager, a radio frequency (RF) device, an infrared (IR) device a Near Field Communication (NFC) device, a Personal Digital Assistant (PDA), a handheld computer, a tablet computer, a phablet, a laptop computer, a set top box, a wearable computer, smart watch, an integrated or distributed device combining various features, such as features of the forgoing devices, or the like.

In some embodiments, as discussed below, the client device can also be, or can communicatively be coupled to, any type of known or to be known medical device (e.g., any type of Class I, II or III medical device), such as, but not limited to, a MRI machine, CT scanner, Electrocardiogram (ECG or EKG) device, wearable neurostimulation device, and the like, or some combination thereof.

In some embodiments, as discussed below, the client device can be part of the system or components discussed in reference to FIGS. 1-2B, and/or the FIGS. 3A-3B.

FIG. 1A is a schematic diagram of a first embodiment therapeutic system 100. Therapeutic system 100 provides one or more outputs that a person wearing the therapeutic system may experience as auditory, visual, and/or tactile stimulus. Thus, in one embodiment, therapeutic system may comprise a left light source 110L, a right light source 110R, a left vibration source 120L, a right vibration source 120R, and a controller 130 for independently controlling and coordinating the action of the light and vibration sources. Thus, for example, therapeutic system 100 may be positioned on the head of a user with left light source 110L positioned over the left eye to provide a left visual stimuli, right light source 110R positioned over the right eye to provide a right visual stimuli, left vibration source 120L positioned to provide left ear auditory stimuli, and right vibration source 120R positioned to provide right ear auditory stimuli.

In one embodiment, left and right light sources 110L, 110R may each comprise light-emitting diodes, an incandescent light source having a wavelength filter, a fluorescent light source, a backlit LCD panel, or other light source configured to provide to the user light at a desired, predetermined wavelength or wavelength range.

In another embodiment, left and right vibration sources 120L, 120R may each comprise earbuds, miniature speakers, or other vibration sources that can provide auditory stimuli to a user. In certain other embodiments, left and right vibration sources 120L, 120R may comprise bone conduction transducers in the audible frequency range to provide vibrations to the user's skull bone that is sensed as auditory by the user's ear. Optionally, one or more of left and right vibration sources 120L, 120R may also produce vibrations that are sensed as tactile stimuli. Thus, for example, controller 130 may provide first signals to bone conduction transducers that vibrate or oscillate at a first frequency that can be interpreted by the user as auditory stimuli and may provide second signals at a second, lower frequency that can be interpreted as a tactile sensation by the user. In other words, bone conduction transducers may be adapted to provide both auditory and tactile stimulus to the user.

In certain embodiments, left and right vibration sources 120L, 120R provide output at specific one or more frequencies or a range of frequencies, and are turned on and off at a stimulation frequency. Thus, for example, a vibration source may be programmed to provide an output at an audio frequency of 256 Hz for some period of time, followed by no output for the following period of time. Thus, the vibration source is the product of an audio frequency and a square wave.

Figure 1B:
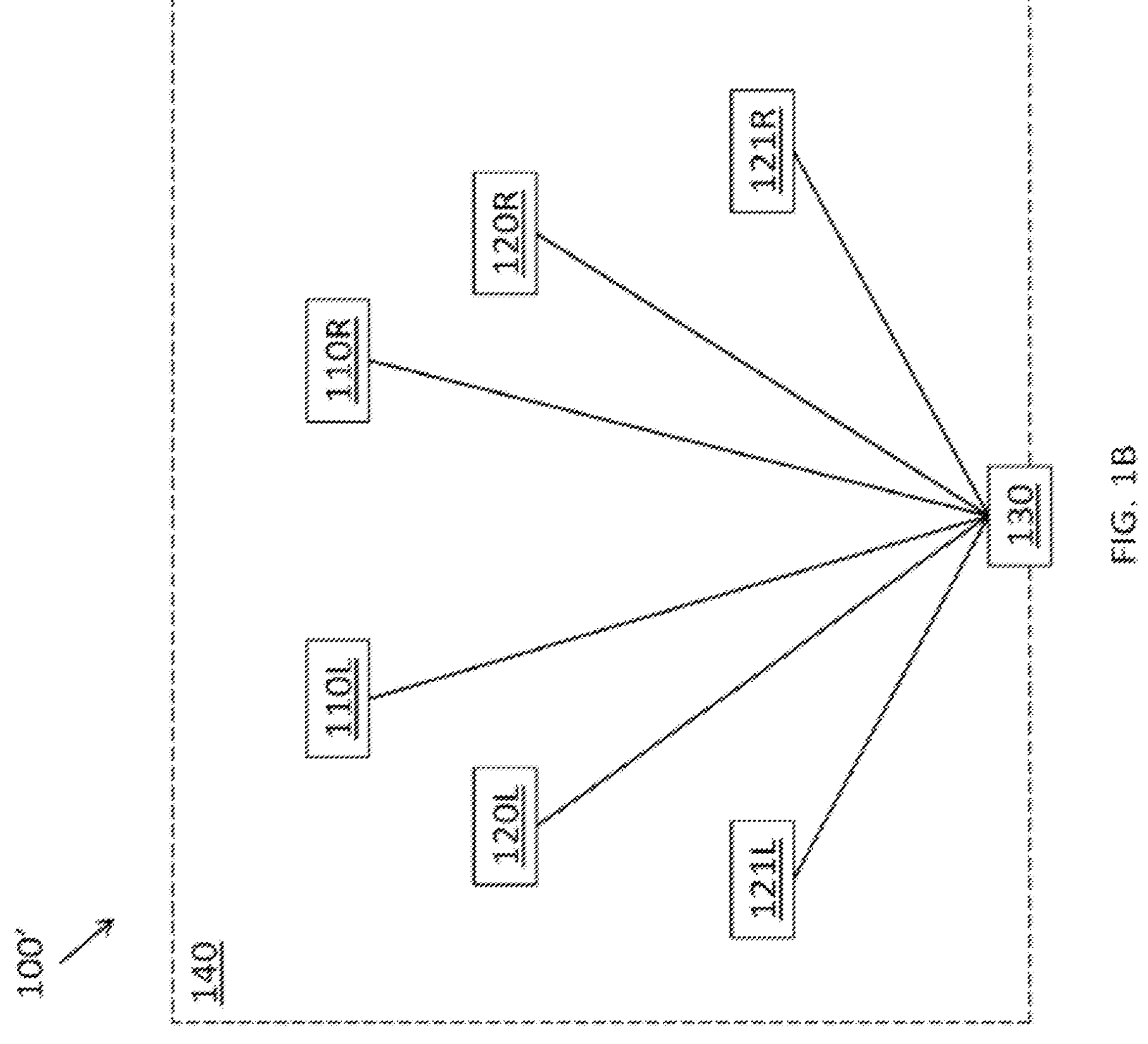

FIG. 1B is a schematic diagram of a second embodiment therapeutic system 100'. Second embodiment therapeutic system 100' is generally similar to first embodiment therapeutic system 100', except as explicitly noted. Specifically, second embodiment therapeutic system 100' includes a left tactile stimulus source 121L and a right tactile stimulus source 121R, each of which may be individually controlled and coordinated with the controller 130 to provide tactile stimuli to a user of therapeutic system 100'.

Figure 2A:
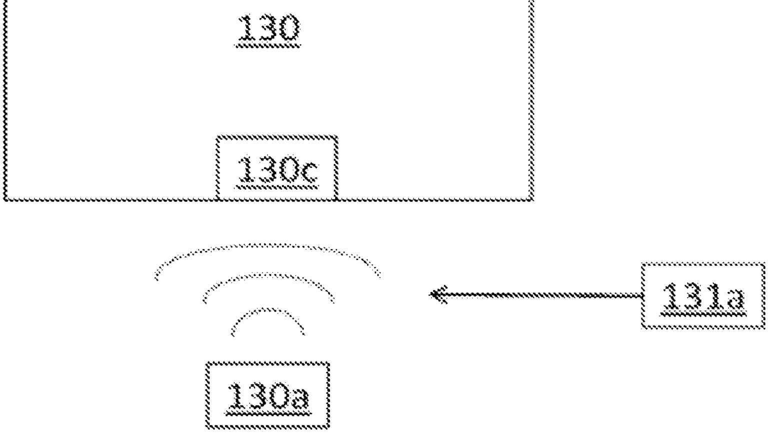
FIGS. 2A and 2B show schematic diagrams of the controller for the therapeutic systems of FIGS. 1A and 1B.
Figure 2B:
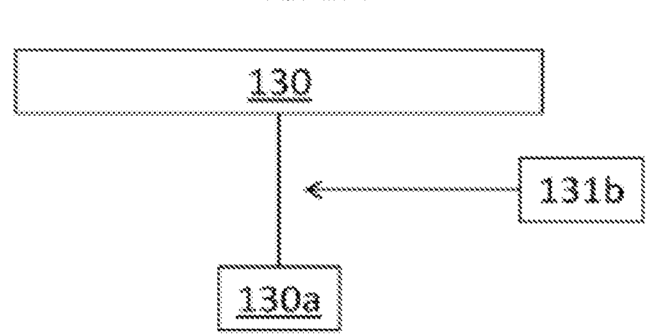

FIGS. 2A and 2B show schematic diagrams of the controller 130 of therapeutic system 100 or 100'. As shown in FIG. 2A, therapeutic system 100 or 100' may optionally include an external control unit 130*a* that may wirelessly communicate with a wireless receiver/transmitter 130*c* of the controller 130 through a wireless connection 131*a*. The wireless connection 131*a* may comprise a Bluetooth connection, a Bluetooth LE connection, a WiFi connection, a ZigBee connection, an infrared (IR) connection, a radiofrequency (RF) connection, or an inaudible auditory signal connection, to name a few examples. The external control unit 130*a* may comprise a custom-built, electronic controller. In many embodiments, the external control unit 130*a* may comprise a personal computing device of the user that may have downloaded onto and operating, a custom computer application or "app" to operate the system 100 or 100' to provide a therapeutic regimen. For example, the personal computing device may comprise a personal computer, a personal laptop computer, a tablet computer, or a smartphone. The custom computer application or "app" may be an application or "app" downloadable from an application distribution platform. The application may include one or more therapeutic regimens that the user may select for implementation by the therapeutic system 100 or 100'. In some embodiments, the application may allow the user to provide feedback information about the efficacy of the therapeutic regimen(s), the feedback may be uploaded and collected by a central server(s) in communication with the application, and the therapeutic regimen(s) may be improved or optimized based on the feedback from the one or more users. Alternatively or in combination, as shown in FIG. 2B, the system 100 or 100' may further comprise an external control unit 130*a*, such as a custom-built controller, that may communicate with the controller 130 through a wired connection 131*a*, for example, a USB, FireWire, or Lightning connection, to name a few examples.

Figure 3A:
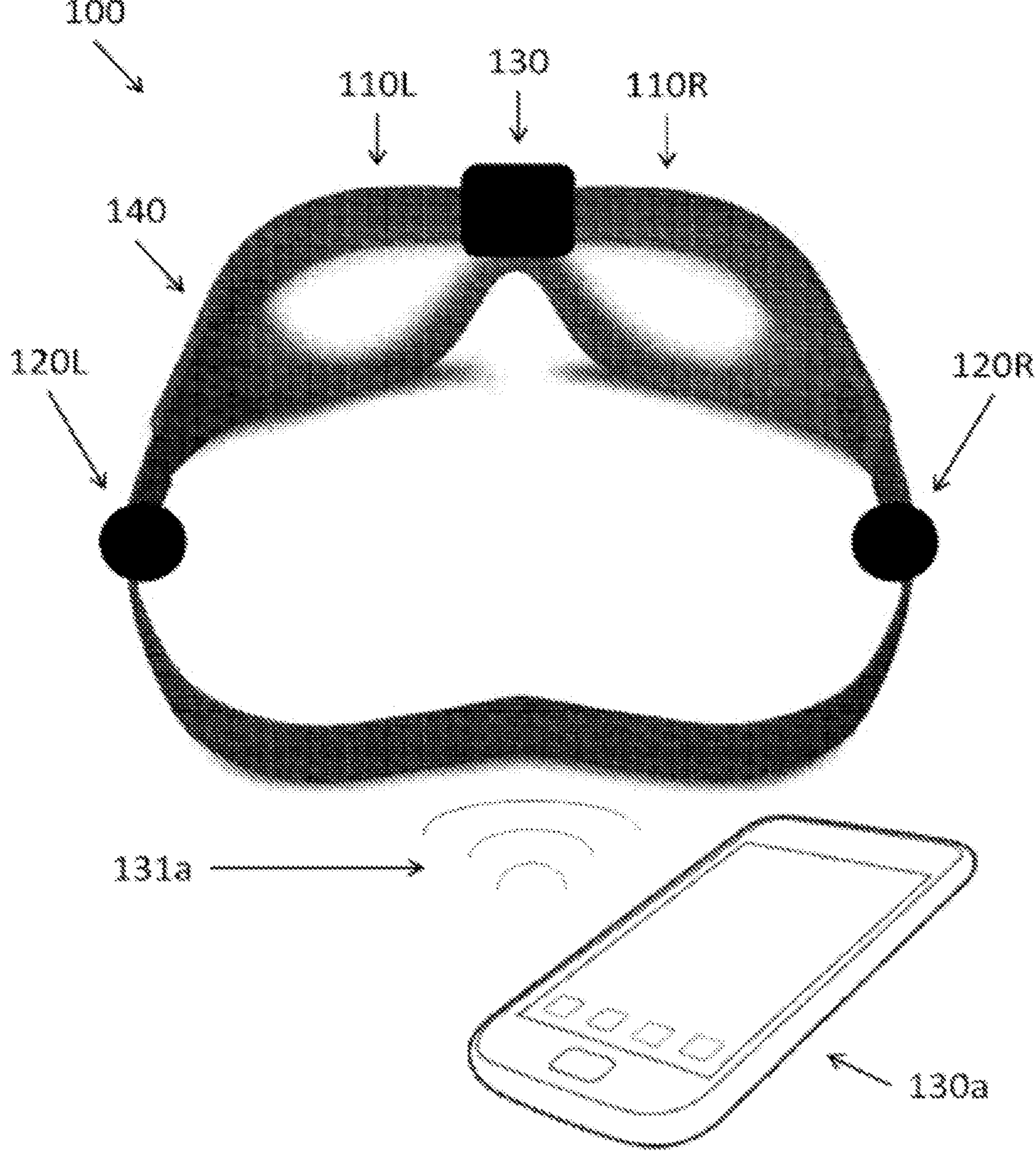
FIG. 3A shows an exemplary therapeutic wearable headset or sleep mask, according to some embodiments of the present disclosure.
Figure 3B:
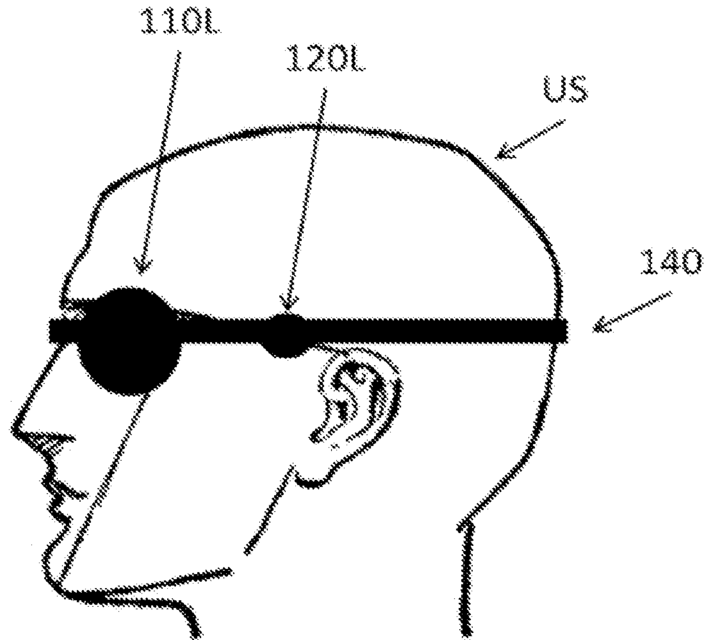
FIG. 3B shows a user wearing the therapeutic wearable headset and sleep mask of FIG. 3A.

FIG. 3A shows one embodiment of the therapeutic system 100 as including therapeutic wearable headset or sleep mask 140 which integrates the light, vibration, and, optionally, tactile sources into a single form factor for presentation to a user. Thus, for example, when a user places wearable headset or sleep mask 140 on their head, left light source 110L is positioned over the left eye to provide a left visual stimuli, right light source 110R is positioned over the right eye to provide a right visual stimuli, left vibration source 120L is positioned to provide left ear auditory stimuli, and right vibration source 120R is positioned to provide right ear auditory stimuli.

As discussed above and herein, the left vibration source 120L and the right vibration source 120R may each comprise bone conduction transducer that may provide both auditory and tactile stimulus. Alternatively, wearable headset or sleep mask 140 is therapeutic system 100' which includes left tactile stimulus source 121L and right tactile stimulus source 121R, each of which may be individually controlled and coordinated with the controller 130, as described above regarding FIG. 1B.

As discussed above and herein, the therapeutic wearable headset or sleep mask 140 may be operated with an external controller 130*a* (e.g., a smartphone) in communication with the controller 130 through a wireless connection 131*a*, for example. The user US may have an option to turn tactile stimulation on or off, for example. FIG. 3B shows a user US wearing the therapeutic wearable headset or sleep mask 140.

Figure 4:
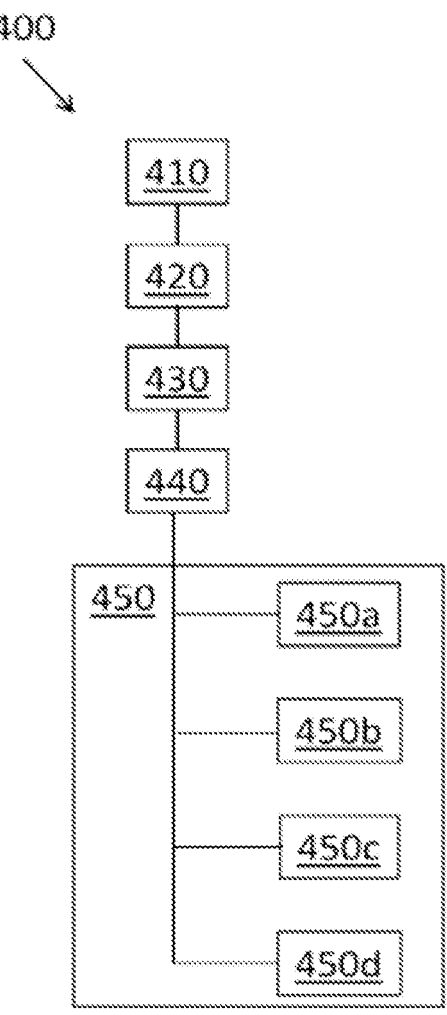
FIG. 4 shows a flow chart of a therapeutic method of providing therapeutic auditory, visual, and/or tactile stimulus, according to some embodiments of the present disclosure.

FIG. 4 shows a flow chart of an exemplary therapeutic method 400 for providing therapeutic auditory, visual, and/or tactile stimulus. In a step 410, a subject having a neurological disorder or condition may be identified. Examples of neurological disorders may include, but are not limited to, insomnia, post-traumatic stress disorder (PTSD), brain injuries such as traumatic brain injury (TBI), mild traumatic brain injury (mTBI), or injuries to the brain due to oxygen deprivation, such as strokes, depression, anxiety, mood disorders, personality disorders, eating disorders, and psychotic disorders. Alternatively, a subject may be selected to undergo a therapeutic method 400 for the purpose of performance enhancement of mental and/or physical tasks for to aid the subject in napping or sleeping. In a step 420, the subject may be provided the therapeutic system or headwear, such as the system 100 or 100' described above. In a step 430, the subject may wear the therapeutic system or headwear, such as wearable headset or sleep mask 140. In a step 440, headset 140 executes programming 450 provided in controller 130 to provide stimuli to the subject. The programming provides two or more of auditory, video, and/or tactile stimulus are concurrently provided by headset 140 to the subject, and thus, for example, may provide power to activate left light source 110L, right light source 110R, left vibration source 120L and or right vibration source 120R.

As discussed above and herein, the left vibration source 120L and the right vibration source 120R may each comprise bone conduction transducer that may provide both auditory and tactile stimulus. Alternatively, wearable headset or sleep mask 140 is therapeutic system 100' which includes left tactile stimulus source 121L and right tactile stimulus source 121R, each of which may be individually controlled and coordinated with the controller 130, as described above regarding FIG. 1B.

In certain embodiments, providing two or more of auditory, video, and/or tactile stimulus concurrently may provide improved therapeutic benefits as compared to providing only one of auditory, video, or tactile stimulus at one time. The two or more auditory, video, and/or tactile stimulus may thus combine to provide the improved therapeutic benefits, for example (i.e., the two or more auditory, video, and/or tactile stimulus may synergize in a way to provide improved results over providing two of the stimuli individually.)

Exemplary instructions for providing stimuli may be provided, for example, by programming 450, such as a subroutine 450*a*, which includes the simultaneous activation of all active auditory, video, and/or tactile stimulus sources. Optionally, the activation of all sources may include the activation of tactile stimulation to run throughout all subsequent auditory and/or visual stimulation. Another exemplary subroutine 450*b* may comprise alternating the left auditory, video, and/or tactile stimulus sources with the right auditory, video, and/or tactile stimulus sources (i.e., the left stimuli and right stimuli take turns being active.) Another exemplary subroutine 450*c* may comprise alternating the visual sources with the auditory and/or tactile sources (i.e., the visual stimuli and the auditory/tactile stimuli take turns being active.) Another exemplary subroutine 450*d* may comprise alternating the left auditory and/or tactile source and the right visual source with the right auditory and/or tactile source and the left visual source (i.e., opposite auditory/tactile stimuli take turns being active.) Such programming is further described below.

In step 440, programming 450, including by not limited to subroutines 450*a*, 450*b*, 450*c*, and 450*d*, may each be applied one or more times, individually or in combination with one another. The programming may, in addition, provide sequences of output in subroutines 450*a*, 450*b*, 450*c*, and 450*d* at different frequencies and/or timings. Thus for example the subroutines may provide output at specific frequencies that change as the subroutine is repeated. Thus for example, subroutine 450*a* may provide auditory output to vibration source 120R or 120L at a frequency of 256 Hz that is turned on and off, that is it is pulsed, at a pulse frequency of 1 Hz for 2 minutes. This square pulse auditory signal thus generates signals at a frequency of 1 Hz in addition to higher harmonics. At a subsequent time the output at 256 Hz is pulsed at twice the previous pulse frequency for 2 minutes. In this manner, the auditory frequency of 256 Hz may be modulated over a wide range, including frequencies corresponding to brain wave frequencies.

In addition, by alerting the output between left and right channels, the brain may be stimulated in a way that it is forced to communicate between the left and right sides of the brain. This forced communication, for example, can allow PTSD memories to be wired to both sides of the brain, thereby stopping undesirable flashbacks.

Although the above steps show method 400 of treating a patient in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the treatment.

One or more of the steps of the method 400 may be performed with the circuitry as described herein, for example, circuitry of the controller 130 or the external control unit 130*a* such as one or more of a processor or logic circuitry such as a central processing unit (CPU) or a programmable array logic for field programmable gate array. The circuitry may be programmed to provide one or more of the steps of the method 400, and the program may comprise program instructions stored on a computer readable memory or programmed steps of the logic circuitry such as the programmable array logic or the field programmable gate array, for example.

EXAMPLE 1

The following describes an example of a stimulation pattern that has been found by empirical studies to be effective for inducing sleep, including napping, increasing neuroplasticity, treating brain injuries from strokes, TBI, or mTBI, improving balance, including improving fine motor control and reaction times, and treating PTSD, to name a few indications.

Light and auditory stimulus at a first frequency may be provided for a first time segment, then at a second lower frequency for a second time segment, and then at a third lower frequency for a third time segment. Each time segment may include one or more sub-segments of light and auditory stimulus, each sub-segment comprising one of the subroutines described above, for example. The light and auditory stimulus may end after a pre-determined time period, such as 20 minutes. The light and auditory stimulus may be ramped back up (i.e., starting from the third frequency, then transitioning to the second frequency, and finally transitioning to the third frequency), such as to wake the user. Alternatively or in combination, the light and auditory stimulus may be maintained at the second frequency such as to maintain a sleep state of the user. As described above, tactile stimulus may be provided concurrently with the auditory stimulus. The light may be provided at a wavelength of 580 nm and the auditory having a frequency of 256 Hz may be provided, or any of a number of auditory frequencies or combinations thereof that the subject can select as they wish.

Table 1 below describes an exemplary treatment regimen for this example. The stimulation provided in Table 1 first cycles through a block of four Segment A outputs, then cycles through a block of four Segment B outputs, then cycles through seven blocks of four Segment C outputs, and lastly repeats the block of four Segment A outputs. For Segment A outputs (A1, A2, A3, and A4), the auditory and light outputs cycle 115 or 116 times between being on for 0.1277 seconds and then being off for 0.1277 seconds (that is, at a pulse frequency of 3.9 Hz), followed by no output for 0.5 seconds. For Segment B outputs (B1, B2, B3 and B4), the auditory and light outputs cycle 44 or 45 times between being on for 0.3333 seconds and then being off for 0.3333 seconds (that is, at a pulse frequency of 1.5 Hz) followed by no output for 0.5 seconds. For Segment C outputs (C1, C2, C3 and C4), the auditory and light outputs cycle 14 or 15 times between being on for 1 second and then being off for 1 second (that is, a pulse frequency of 0.5 Hz), followed by no output for 1 second. Segments A1, B1, and C1 pulse the right and left sides of both the light and auditory together, with all outputs are synchronized to be on or off at the same time, as provided by subroutine 450*a*. Segments A2, B2, and C2 synchronize the left side light and auditory output, and the right side light and auditory output to be opposite to one another, as provided by subroutine 450*b*. Segments A3, B3, and C3 synchronize both lights together to be opposite to both auditory outputs, as provided by subroutine 450*c*. Segments A4, B4, and C4 synchronize the right auditory and light to be opposite to the left auditory and light outputs, as provided by subroutine 450*d*.

TABLE 1

| | Auditory Left | Auditory Right | Light Left | Light Right |
|---|---|---|---|---|
| Segments A1-A4 for 120 s | | | | |
| Segment A1 (Light and Auditory both side spulse together)<br>Repeat 116 times, followed by 0.5 sec gap | On 0.1277 s<br>Off 0.1277 s | On 0.1277 s<br>Off 0.1277 s | On 0.1277 s<br>Off 0.1277 s | On 0.1277 s<br>Off 0.1277 s |
| Segment A2 (light and auditory on left side, alternating light and auditory on Right).<br>Repeat 116 times, followed by 0.5 sec gap | On 0.1277 s<br>Off 0.1277 s | Off 0.1277 s<br>On 0.1277 s | On 0.1277 s<br>Off 0.1277 s | Off 0.1277 s<br>On 0.1277 s |
| Segment A3 (both lights together, alternating with both auditories together)<br>Repeat 115 times, followed by 0.5 sec gap | On 0.1277 s<br>Off 0.1277 s | On 0.1277 s<br>Off 0.1277 s | Off 0.1277 s<br>On 0.1277 s | Off 0.1277 s<br>On 0.1277 s |
| Segment A4 (auditory left and light right together, alternating auditory right and light left together)<br>Repeat 115 times, followed by 0.5 sec gap | On 0.1277 s<br>Off 0.1277 s | Off 0.1277 s<br>On 0.1277 s | Off 0.1277 s<br>On 0.1277 s | On 0.1277 s<br>Off 0.1277 s |
| Segments B1-B4 for 120 s | | | | |
| Segment B1 (Light and Auditory both sides pulse together)<br>Repeat 45 times, followed by 0.5 sec gap | On 0.3333 s<br>Off 0.3333 s | On 0.3333 s<br>Off 0.3333 s | On 0.3333 s<br>Off 0.3333 s | On 0.3333 s<br>Off 0.3333 s |
| Segment B2 (light and auditory on left side, alternating light and auditory on Right)<br>Repeat 44 times, followed by 0.5 sec gap | On 0.3333 s<br>Off 0.3333 s | Off 0.3333 s<br>On 0.3333 s | On 0.3333 s<br>Off 0.3333 s | Off 0.3333 s<br>On 0.3333 s |
| Segment B3 (both lights together, alternating with both auditories together)<br>Repeat 44 times, followed by 0.5 sec gap | On 0.3333 s<br>Off 0.3333 s | On 0.3333 s<br>Off 0.3333 s | Off 0.3333 s<br>On 0.3333 s | Off 0.3333 s<br>On 0.3333 s |
| Segment B4 (auditory left and light right together, alternating auditory right and light left together)<br>Repeat 44 times, followed by 0.5 sec gap | On 0.3333 s<br>Off 0.3333 s | Off 0.3333 s<br>On 0.3333 s | Off 0.3333 s<br>On 0.3333 s | On 0.3333 s<br>Off 0.3333 s |
| Repeat the following Segments C1-C4 7 times for a total of 14 minutes | | | | |
| Segment C1 (Light and Auditory both sides pulse together)<br>Repeat 15 times, followed by 1 sec gap | On 1 sec<br>Off 1 sec | On 1 sec<br>Off 1 sec | On 1 sec<br>Off 1 sec | On 1 sec<br>Off 1 sec |
| Segment C2 (light and auditory on left side, alternating light and auditory on Right)<br>Repeat 15 times, followed by 1 sec gap | On 1 sec<br>Off 1 sec | Off 1 sec<br>On 1 sec | On 1 sec<br>Off 1 sec | Off 1 sec<br>On 1 sec |
| Segment C3 (both lights together, alternating with both auditories together)<br>Repeat 14 times, followed by 1 sec gap | On 1 sec<br>Off 1 sec | On 1 sec<br>Off 1 sec | Off 1 sec<br>On 1 sec | Off 1 sec<br>On 1 sec |

TABLE 1-continued

| | Auditory Left | Auditory Right | Light Left | Light Right |
|---|---|---|---|---|
| Segment C4 (auditory left and light right together, alternating auditory right and light left together) Repeat 14 times, followed by 1 sec gap | On 1 sec<br>Off 1 sec<br>Off 1 sec | Off 1 sec<br>On 1 sec<br>On 1 sec | Off 1 sec<br>On 1 sec<br>On 1 sec | On 1 sec<br>Off 1 sec<br>Off 1 sec |
| Segments A1-A4 for 120 s | | | | |
| Segment A1 (Light and Auditory both sides pulse together) Repeat 116 times, followed by 0.5 sec gap | On 0.1277<br>Off 0.1277 | On 0.1277<br>Off 0.1277 | On 0.1277<br>Off 0.1277 | On 0.1277<br>Off 0.1277 |
| Segment A2 (light and auditory on left side, alternating light and auditory on Right) Repeat 116 times, followed by 0.5 sec gap | On 0.1277<br>Off 0.1277 | Off 0.1277<br>On 0.1277 | On 0.1277<br>Off 0.1277 | Off 0.1277<br>On 0.1277 |
| Segment A3 (both lights together, alternating with both auditories together) Repeat 115 times, followed by 0.5 sec gap | On 0.1277<br>Off 0.1277 | On 0.1277<br>Off 0.1277 | Off 0.1277<br>On 0.1277 | Off 0.1277<br>On 0.1277 |
| Segment A4 (auditory left and light right together, alternating auditory right and light left together) Repeat 115 times, followed by 0.5 sec gap | On 0.1277<br>Off 0.1277 | Off 0.1277<br>On 0.1277 | Off 0.1277<br>On 0.1277 | On 0.1277<br>Off 0.1277 |

EXAMPLE 2

The following describes an example of a stimulation pattern that has been found by empirical studies to be effective for inducing sleep. The stimulation pattern of Example 2 includes the part of the treatment regimen shown in Table 1. Specifically, the stimulation first cycles through a block of four Segment A outputs, then cycles through a block of four Segment B outputs, and then cycles through seven blocks of four Segment C outputs. The repetition of the last block of four Segment A outputs is not provided in Example 2.

EXAMPLE 3

The following described example of a stimulation pattern that has been found by empirical studies to be effective for increasing alpha wave brain activity, inducing neuroplasticity, treating stroke or other brain injuries such as TBI, mTBI, including improving balance, improving fine motor control and reaction times, and treating PTSD, to name a few indications.

In this example, the four subroutines described above and herein are applied and repeated for multiple time segments, each at a predetermined stimulation (repetition) frequency. The four subroutines may be repeated, such as with each segment of the four subroutines lasting 120 seconds, for example. As described above, tactile stimulus may be provided concurrently with the auditory stimulus. The light may be provided at a wavelength of 580 nm and the auditory having a frequency of 432 Hz may be provided.

Table 2 below describes an exemplary treatment regimen for this example. The stimulation provided in Table 2 cycles through a block of four Segment A outputs 10 times. For Segment A1, A2, A3, and A4, the auditory and light outputs cycle 115 or 116 times between being on for 0.1277 seconds and then being off for 0.1277 seconds, followed by no output for 0.5 seconds. Segments A1 pulses the right and left sides of both the light and auditory together, with all outputs are synchronized to be on or off at the same time, as provided by subroutine 450*a*. Segment A2 synchronizes the left side light and auditory output, and the right side light and auditory output to be opposite to one another, as provided by subroutine 450*b*. Segment A3 synchronizes both lights together to be opposite to both auditory outputs, as provided by subroutine 450*c*. Segment A4 synchronizes the right auditory and light to be opposite to the left auditory and light outputs, as provided by subroutine 450*d*.

TABLE 2

| Repeat the following Segments A1-A4 10 times for a total time of 20 minutes | Auditory Left | Auditory Right | Light Left | Light Right |
|---|---|---|---|---|
| Segment A1 (Light and Auditory both sides pulse together) Repeat 116 times, followed by 0.5 sec gap | On 0.1277 s<br>Off 0.1277 s | On 0.1277 s<br>Off 0.1277 s | On 0.1277 s<br>Off 0.1277 s | On 0.1277 s<br>Off 0.1277 s |

TABLE 2-continued

| Repeat the following Segments A1-A4 10 times for a total time of 20 minutes | Auditory Left | Auditory Right | Light Left | Light Right |
|---|---|---|---|---|
| Segment A2 (light and auditory on left side, alternating light and auditory on Right) Repeat 116 times, followed by 0.5 sec gap | On 0.1277 s<br>Off 0.1277 s | Off 0.1277 s<br>On 0.1277 s | On 0.1277 s<br>Off 0.1277 s | Off 0.1277 s<br>On 0.1277 s |
| Segment A3 (both lights together, alternating with both auditories together) Repeat 115 times, followed by 0.5 sec gap | On 0.1277 s<br>Off 0.1277 s | On 0.1277 s<br>Off 0.1277 s | Off 0.1277 s<br>On 0.1277 s | Off 0.1277 s<br>On 0.1277 s |
| Segment A4 (auditory left and light right together, alternating auditory right and light left together) Repeat 115 times, followed by 0.5 sec gap | On 0.1277 s<br>Off 0.1277 s | Off 0.1277 s<br>On 0.1277 s | Off 0.1277 s<br>On 0.1277 s | On 0.1277 s<br>Off 0.1277 s |

EXAMPLE 4

The following described yet another example of a stimulation pattern that has been found by empirical studies to be effective for increasing energy levels in the subject. Light and auditory stimulus at a first frequency may be provided for a first time segment, then at a second higher frequency for a second time segment, then back at the first frequency for a subsequent time segment, and so forth. Each time segment may include one or more sub-segments of light and auditory stimulus, each sub-segment comprising one of the subroutines described above, for example. The light and auditory stimulus may end after a pre-determined time period, such as 20 minutes. As described above, tactile stimulus may be provided concurrently with the auditory stimulus. The light may be provided at a wavelength of 580 nm and the auditory having a frequency of 432 Hz may be provided.

Table 3 below describes an exemplary treatment regimen for this example. The stimulation provided in Table 3 cycles ten times first through a block of four Segment A outputs, then through a block of four Segment D outputs. For Segment A outputs (A1, A2, A3, and A4), the auditory and light outputs cycle 115 or 116 times between being on for 0.1277 seconds and then being off for 0.1277 seconds, followed by no output for 0.5 seconds. For Segment D outputs (D1, D2, D3 and D4), the auditory and light outputs cycle 44 or 45 times between being on for 0.0667 seconds and then being off for 0.0667 seconds, followed by no output for 0.5 seconds. Segments A1 and D1 pulse the right and left sides of both the light and auditory together, with all outputs are synchronized to be on or off at the same time, as provided by subroutine 450*a*. Segments A2 and D2 synchronize the left side light and auditory output, and the right side light and auditory output to be opposite to one another, as provided by subroutine 450*b*. Segments A3 and D3 synchronize both lights together to be opposite to both auditory outputs, as provided by subroutine 450*c*. Segments A4 and D4 synchronize the right auditory and light to be opposite to the left auditory and light outputs, as provided by subroutine 450*d*.

TABLE 3

| Repeat 10 times: Segments A1-A4 followed by Segments D1-D4, for a total time of 20 minutes | Auditory Left | Auditory Right | Light Left | Light Right |
|---|---|---|---|---|
| Segment A1 (Light and Auditory both sides pulse together) Repeat 116 times, followed by 0.5 sec gap | On 0.1277 s<br>Off 0.1277 s | On 0.1277 s<br>Off 0.1277 s | On 0.1277 s<br>Off 0.1277 s | On 0.1277 s<br>Off 0.1277 s |
| Segment A2 (light and auditory on left side, alternating light and auditory on Right) Repeat 116 times, followed by 0.5 sec gap | On 0.1277 s<br>Off 0.1277 s | Off 0.1277 s<br>On 0.1277 s | On 0.1277 s<br>Off 0.1277 s | Off 0.1277 s<br>On 0.1277 s |
| Segment A3 (both lights together, alternating with both auditories together) Repeat 115 times, followed by 0.5 sec gap | On 0.1277 s<br>Off 0.1277 s | On 0.1277 s<br>Off 0.1277 s | Off 0.1277 s<br>On 0.1277 s | Off 0.1277 s<br>On 0.1277 s |
| Segment A4 (auditory left and light right together, alternating auditory right and light left together) Repeat 115 times, followed by 0.5 sec gap | On 0.1277 s<br>Off 0.1277 s | Off 0.1277 s<br>On 0.1277 s | Off 0.1277 s<br>On 0.1277 s | On 0.1277 s<br>Off 0.1277 s |

TABLE 3-continued

| Repeat 10 times: Segments A1-A4 followed by Segments D1-D4, for a total time of 20 minutes | Auditory Left | Auditory Right | Light Left | Light Right |
|---|---|---|---|---|
| Segment D1 (Light and Auditory both sides pulse together) Repeat 221 times, followed by 0.5 sec gap | On 0.0667 s Off 0.0667 s | On 0.0667 s Off 0.0667 s | On 0.0667 s Off 0.0667 s | On 0.0667 s Off 0.0667 s |
| Segment D2 (light and auditory on left side, alternating light and auditory on Right) Repeat 221 times, followed by 0.5 sec gap | On 0.0667 s Off 0.0667 s | Off 0.0667 s On 0.0667 s | On 0.0667 s Off 0.0667 s | Off 0.0667 s On 0.0667 s |
| Segment D3 (both lights together, alternating with both auditories together) Repeat 221 times, followed by 0.5 sec gap | On 0.0667 s Off 0.0667 s | On 0.0667 s Off 0.0667 s | Off 0.0667 s On 0.0667 s | Off 0.0667 s On 0.0667 s |
| Segment D4 (auditory left and light right together, alternating auditory right and light left together) Repeat 221 times, followed by 0.5 sec gap | On 0.0667 s Off 0.0667 s | Off 0.0667 s On 0.0667 s | Off 0.0667 s On 0.0667 s | On 0.0667 s Off 0.0667 s |

EXAMPLE 5

The following Table 4 lists experimental results for the use of the inventive methods. The table lists what was being tested or treated, details of the conditions, the number of subjects, and the results of the tests. In each case, the stimulation in Example 1 for treating non-sleep related problems and for inducing a short sleep, and the stimulation in Example 2 was used for all other treatments.

Several of the treatments provided improvements in physical and/or mental performance, such as improving fine motor control and reaction times. This may be due to the device providing improved neuroplasticity in the days after treatment. Other treatments provided improvements in performing tasks and recovery from brain injury, such as injuries resulting from oxygen deprivation (strokes) and for those suffering from traumatic brain injury (TBI) or mild traumatic brain injury, and my provide improving balance, improving fine motor control. Other treatments provided relief to sufferers of PTSD by reducing the subject's response to triggering stimuli.

TABLE 4

| Treatment For | Details | No. of subjects | Results |
|---|---|---|---|
| Pain Management | Reduction of chronic nerve damage pain and improvement of sleep on self. Use of device for 3 months with 20 min/day of use of device | 1 | Eliminated chronic nerve damage pain for the time the device was used. |
| PTSD | Treating PTSD. Device use time of 5 hours. | 3 | Reduced flashbacks, nightmares and hypervigilance in all 3 subjects |
| Performance Enhancement | Marksmanship (rifles and pistols), endurance and speed driving (advanced surveillance, coordination and evasion). 6 hours training each subject. | 20 | Significant improvements in marksmanship in all participants and ease of concentration during speed driving, faster times on endurance trials for 19/20 subjects |
| Performance Enhancement | Fine motor skills on bomb disposal personnel 3 hours training with device | 3 | Improved performance of fine motor skills on bomb disposal VR simulation for all subjects |
| Performance Enhancement | Fine motor skills of surgeons- 3 hours training each | 3 | Improved performance of fine motor skills on surgical procedures VR simulation for all subjects. |

TABLE 4-continued

| Treatment For | Details | No. of subjects | Results |
|---|---|---|---|
| Performance Enhancement | Pistol use and marksmanship. 3 hours training | 2 | 10% and 30% respectively increased speed in stripping and reassembling weapons. (average each of 5 tests, pre and post training) 6% average improvement in marksmanship scores - highly significant for such level of skill for all subjects |
| Performance Enhancement and PTSD | Performance by anti-terror and anti-drug squads of an elite firearms unit of a police force. 3 hours training each. | 5 | 10% average improvement in scores. Total absence of any PTSD |
| Performance Enhancement | Marksmanship. 2 hours training | 1 | average grouping shrunk from 5 inches to 1 inch at 200 yds. |
| Brain State | Increasing alpha activity. 4 hours total training time per subject. Group 1 L&S stimulation and biofeedback. Group 2 - just L&S stimulation Group 3 just biofeedback, Group 4 control. Double blinded - those administering had no idea of what was predicted to happen | 20 | Results as predicted. Group 1 greatest change, followed by group 2, Group 3 least change of active groups. Group 4 no change. |
| Performance Enhancement | Marksmanship. | 3 + 15 | Significant improvement for all subjects. |
| Mental Performance Enhancement | Attention, learning and resistance to interrogation - 4 hours each person. Conduct after Capture course. | 3 | positive reports from all subjects |
| Performance Enhancement | Motion sickness for fixed wing aircraft pilots who have developed problems. 4 hours training per subject | 4 | Dramatic improvements in half of subjects. Small improvements in remaining half of subjects |
| PTSD | PTSD symptoms - test to remove neurological symptoms of flashbacks, nightmares and cold sweats | 33 | Successful in 31/33 subjects |
| Performance Enhancement | Driver performance using VR simulators for reaction speeds and performance under stress | 2 | Immediate increase in reaction speeds and improved performance for all subjects |
| Performance Enhancement | Professional soccer player performance. Trained for 4 hours. Battery of 21 tests | 1 | 5-25% increase in speeds to complete tests |
| Inducing Sleep | Sleep patterning and circadian rhythm adjustment for crews setting endurance records. members each year. Also used for improving safety drills when parachuting | 6 | All subjects fell asleep using the device during training, including one subject that was ill with a virus and couldn't otherwise sleep. |
| Performance Enhancement | Race car driver performance. Ten days of training for 30 minutes per day. | 1 | Subject won his first Grand Prix of the season. |
| Performance Enhancement | Soccer player kicking performance. 5 days of 1 hour each day | 1 | Subject went from 5th ranked to highest ranked |

TABLE 4-continued

| Treatment For | Details | No. of subjects | Results |
|---|---|---|---|
| Stroke Recovery | Use on 6 year post stroke subjects. four hours training. | 10 | Observable balance improvement in 7/10 subjects. 3 subjects had had dramatic improvements in their sleep. |
| Epilepsy Seizure Reduction | Effect on seizures of photosensitive epileptics. 4 hours training | 3 | One subject was found to not be epileptic. The other two subjects had a reduction in both severity and frequency of seizures, for at least a period of at least one month. |
| Concussion Recovery | Effect on concussions | 18 | All subjects appeared to have recovery happen at very fast speed. |
| Performance Enhancement | Effect on musical ability of a jazz musician. | 1 | Greatly improved performance speed |
| PTSD | PTSD. Treatment protocol lasting 3 sessions of 2 hours each | 22 | 19 individuals saw a cessation of major symptoms - flashbacks, nightmares, cold sweats and hypervigilance. the remaining 3 appeared to be calmer after treatment, but did not stop the major neurological symptoms |
| Sleep | Insomnia | 1 | Goes to sleep 4 times in 45 mins |
| Pain Management | Chronic Regional Pain Syndrome | 1 | Subject had constant pain on touching arms with no relief in 3 years Subject saw immediate pain relief on first use of the device. Continued use over the following weeks results in periods of time without pain grow up to four hours following each use. Averaging at two hours. |
| Pain Management and Sleep | Chronic pain | 1 | After six months of use, the subject continues getting 30% more sleep, and a significant reduction in pain. Device continues to be used 3-4 times a week for 20 min. |

EXAMPLE EMBODIMENTS

The following are example embodiments.

An example embodiment 1 comprises a method of providing stimulation to a user, the method comprises: providing a headset to be worn by the user; applying, with the headset, a left visual stimulus pattern to the left eye of the user; applying, with the headset, a right visual stimulus pattern to the right eye of the user; applying, with the headset, a left auditory stimulus pattern to the left side of a head of the user; and applying, with the headset, a right auditory stimulus pattern to the right side of the head, wherein the applications of the left visual stimulus pattern, the right visual stimulus pattern, the left auditory stimulus pattern, and the right auditory stimulus pattern are coordinated with one another.

An example embodiment 2 including example embodiment 1, wherein applying, with the headset, the left auditory stimulus pattern comprises applying, with the headset, a left tactile stimulus pattern, and wherein applying, with the headset, the right auditory stimulus pattern comprises applying, with the headset, a right tactile stimulus pattern.

An example embodiment 3 including example embodiment 2, wherein the left tactile stimulus pattern and the right tactile stimulus pattern are configured to produce a plurality of concurrent left and right tactile signals.

An example embodiment 4 including example embodiment 2, wherein the left tactile stimulus pattern and the right tactile stimulus pattern are configured to produce a plurality of alternating left and right tactile signals.

An example embodiment 5 including example embodiment 2, wherein the left tactile stimulus pattern is coordinated with the left auditory stimulus pattern, and wherein the right tactile stimulus pattern is coordinated with the right auditory stimulus pattern.

An example embodiment 6 including example embodiment 5, wherein the left tactile stimulus pattern comprises a left-side vibration at a first frequency generated concurrently with auditory during the left auditory stimulus pattern, and wherein the right tactile stimulus pattern comprises a right-side vibration at a second frequency generated concurrently with auditory during the right auditory stimulus pattern.

An example embodiment 7 including example embodiment 6, wherein one or more of the left-side or right-side vibration is a vibration of from 0.5 Hz to 1.5 Hz.

An example embodiment 8 including any one of example embodiments 1 through 7, wherein applying, with the headset, the left auditory stimulus pattern comprises generating the left tactile stimulus pattern with a left bone conduction transducer of the headset, and wherein applying, with the headset, the right auditory stimulus pattern comprises generating the left tactile stimulus pattern with a left bone conduction transducer of the headset.

An example embodiment 9 including any one of example embodiments 1 through 7, wherein the left visual stimulus pattern and the right visual stimulus pattern are configured to produce a plurality of concurrent left and right light signals.

An example embodiment 10 including any one of example embodiments 1 through 7, wherein the left visual stimulus pattern and the right visual stimulus pattern are configured to produce a plurality of alternating left and right light signals.

An example embodiment 11 including any one of example embodiments 1 through 7, wherein the left auditory stimulus pattern and the right auditory stimulus pattern are configured to produce a plurality of concurrent left and right auditory signals.

An example embodiment 12 including any one of example embodiments 1 through 7, wherein the left auditory stimulus pattern and the right auditory stimulus pattern are configured to produce a plurality of alternating left and right auditory signals.

An example embodiment 13 including any one of example embodiments 1 through 12, wherein one or more of the left or right visual stimulus pattern has a light wavelength of from 550 nm to 610 nm.

An example embodiment 14 including any one of example embodiments 1 through 13, wherein one or more of the left or right visual stimulus pattern has a light wavelength of 580 nm.

An example embodiment 15 including any one of example embodiments 1 through 14, wherein one or more of the left or right auditory stimulus pattern includes an auditory frequency of from 240 Hz to 480 Hz.

An example embodiment 16 including any one of example embodiments 1 through 15, wherein one or more of the left or right auditory stimulus pattern includes an auditory frequency of 256 Hz or 432 Hz.

An example embodiment 17 including any one of example embodiments 1 through 16, wherein one or more of the left visual stimulus pattern comprises repeatedly pulsing a light at one or more of a first frequency, a second frequency less than the first frequency, or a third frequency less than the first and second frequencies.

An example embodiment 18 including any one of example embodiments 1 through 17, wherein the first frequency is between 3.75 Hz and 4.25 Hz, the second frequency is between 1.25 Hz and 1.75 Hz, and the third frequency is between 0.25 Hz and 0.75 Hz.

An example embodiment 19 including example embodiment 19, wherein the first frequency is 3.9 Hz, the second frequency is 1.5 Hz, and the third frequency is 1 Hz.

An example embodiment 20 including any one of example embodiments 18 and 19, wherein repeatedly pulsing the light comprises pulsing the light for a predetermined time interval.

An example embodiment 21 including example embodiment 20, wherein the predetermined time interval is 25-35 seconds.

An example embodiment 22 including any one of example embodiments 20 and 21, wherein the predetermined time interval is 30 seconds.

An example embodiment 23 including any one of example embodiments 1 through 22, wherein one or more of the left or right auditory stimulus pattern comprises a sequence stimulus patterns each having a pulse frequency having a pulse period, said repeating temporal signals including a portion of the pulse period with including an auditory frequency of from 240 Hz to 480 Hz and a portion of the pulse period.

An example embodiment 24 including example embodiment 23, wherein said portion of said pulse period is one half of the pulse period.

An example embodiment 25 including any one of example embodiments 23 and 24, wherein said sequence of stimulus patterns includes a first stimulus pattern having a first pulse frequency, a second stimulus pattern having a second pulse frequency less than the first pulse frequency, and a third stimulus pattern having a third pulse frequency less than the second pulse frequency.

An example embodiment 26 including example embodiment 25, wherein the first pulse frequency is between 3.75 Hz and 4.25 Hz, the second pulse frequency is between 1.25 Hz and 1.75 Hz, and the third pulse frequency is between 0.25 Hz and 0.75 Hz.

An example embodiment 27 including example embodiment 25 wherein the first pulse frequency is 3.9 Hz, the second pulse frequency is 1.5 Hz, and the third pulse frequency is 1 Hz.

An example embodiment 28 including any one of example embodiments 25 through 27, wherein said first stimulus pattern, said second stimulus pattern, or said third stimulus pattern stimulates for a predetermined time interval.

An example embodiment 29 including example embodiments 28, wherein the predetermined time interval is 25-35 seconds.

An example embodiment 30 including any one of example embodiments 28 and 29, wherein the predetermined time interval is 30 seconds.

An example embodiment 31 including any one of example embodiments 1 through 30, wherein the headset is in operative communication with an external control device.

An example embodiment 32 comprises a method of treating a neurological disease or condition or providing performance enhancement using the method of example embodiment 1.

An example embodiment 33 including example embodiment 32, where said neurological disease or condition comprises insomnia, post-traumatic stress disorder (PTSD), stokes or other brain injuries such as traumatic brain injury (TBI), or mild traumatic brain injury (mTBI).

An example embodiment 34 including example embodiment 32, where said performance enhancement is providing sleep, the improvement of mental capabilities, or the improvement of physical capabilities.

An example embodiment 35 including an apparatus to provide stimulation to a user, the apparatus comprises: a frame configured to be worn on a head of the user; a left light source configured to generate a left visual stimulus pattern; a right light source configured to generate a right visual stimulus pattern; a left auditory source configured to generate a left auditory stimulus pattern; a right auditory source configured to generate a right auditory stimulus pattern; and a controller coupled to the left light source, the right light source, the left auditory source, and the right auditory source, wherein applications of the left visual stimulus pattern, the right visual stimulus pattern, the left auditory stimulus pattern, and the right auditory stimulus pattern are independently controlled from one another but coordinated with one another by the controller.

An example embodiment 36 including example embodiment 35, wherein the left auditory source is further configured to generate a left tactile stimulus pattern, and wherein the right auditory source is further configured to generate a right tactile stimulus pattern.

An example embodiment 37 including any one of example embodiments 35 and 36, wherein one or more of the left or right auditory source comprises a bone conduction transducer.

An example embodiment 38 including any one of example embodiments 35 through 37, wherein the controller is configured to be in communication with and operated by an external control unit.

An example embodiment 39 including example embodiment 38, wherein the external control unit is in wireless communication with the controller.

An example embodiment 40. including any one of example embodiments 38 and 39, wherein the external control unit comprises one or more of a personal computer, a laptop computer, a tablet computer, a smartphone, or a wearable computer.

An example embodiment 41 including any one of example embodiments 38 through 40, wherein the external control unit has operating thereon an application configured to interface with and operate the controller.

An example embodiment 42 including any one of example embodiments 35 through 41, wherein one or more of the left or right light source comprises a light-emitting diode (LED).

An example embodiment 43 including any one of example embodiments 35 through 42, wherein one or more of the left or right light source is configured to generate light at 550-610 nm.

An example embodiment 44 including any one of example embodiments 35 through 42, wherein one or more of the left or right light source is configured to generate light at 580 nm.

An example embodiment 45 comprises a method to provide stimulation to a user, the method comprises: concurrently providing a left-side light stimulus to a left eye of the user, a right-side light stimulus to a right eye of the user, a left-side auditory stimulus to a left side of the user, and a right-side auditory stimulus to a right side of the user for a first time interval; alternating providing the left-side light stimulus and left-side auditory stimulus with providing the right-side light stimulus and right-side auditory stimulus for a second time interval; alternating providing the left-side and right-side light stimuli with providing the left-side and right-side auditory stimuli for a third time interval; and alternating providing the left-side light stimulus and right-side auditory stimulus with providing the right-side light stimulus and left-side auditory stimulus for a fourth time interval.

An example embodiment 46 including example embodiment 45, wherein the second time interval is after the first time interval, the third time interval is after the second time interval, and the fourth time interval is after the third time interval.

An example embodiment 47 including of any one of example embodiments 45 and 46, wherein one or more of the left-side or right-side light stimuli comprises pulsing a light at a predetermined pulsing frequency for one or more of the first, second, third, or fourth time intervals.

An example embodiment 48 including any one of example embodiments 45 through 47, wherein one or more of the left-side or right-side auditory stimuli comprises generating a auditory at a predetermined generation frequency for one or more of the first, second, third, or fourth time intervals.

An example embodiment 49 including any one of example embodiments 45 through 48, wherein the left-side light stimulus, the right-side light stimulus, the left-side auditory stimulus, and the right-side auditory stimulus are generated with a wearable headset.

An example embodiment 50 including any one of example embodiments 45 through 49, further comprises providing a left-side tactile stimulus concurrently with the left-side auditory stimulus and providing a right-side tactile stimulus concurrently with the right-side auditory stimulus.

An example embodiment 51 comprises a method of treating a neurological disease or condition or providing performance enhancement using the method of example embodiment 45.

An example embodiment 52 including example embodiment 51, where said neurological disease or condition comprises insomnia, post-traumatic stress disorder (PTSD), stokes or other brain injuries such as traumatic brain injury (TBI), or mild traumatic brain injury (mTBI).

An example embodiment 53 including example embodiment 51, where said performance enhancement is providing sleep, improving alpha wave activity, the improvement of mental capabilities, or the improvement of physical capabilities.

An example embodiment 54 comprises a method to provide stimulation to a user, the method comprises: providing a headset to be worn by the user; applying, with the headset, a left auditory stimulus pattern to the left side of a head of the user; and applying, with the headset, a right auditory stimulus pattern to the right side of the head, wherein the applications of the left auditory stimulus pattern and the right auditory stimulus pattern are coordinated with one another.

An example embodiment 55 including example embodiment 54, wherein the left auditory stimulus pattern and the right auditory stimulus pattern are configured to produce a plurality of concurrent left and right auditory signals.

An example embodiment 56 including example embodiment 54, wherein the left auditory stimulus pattern and the right auditory stimulus pattern are configured to produce a plurality of alternating left and right auditory signals.

An example embodiment 57 including any one of example embodiments 54 through 56, wherein one or more of the left or right auditory stimulus pattern includes an auditory frequency of from 240 Hz to 480 Hz.

An example embodiment 58 including any one of example embodiments 54 through 57, wherein one or more of the left or right auditory stimulus pattern includes an auditory frequency of 256 Hz or 432 Hz.

An example embodiment 59 including any one of example embodiments 54 through 58, wherein one or more of the left or right auditory stimulus pattern comprises a sequence stimulus patterns each having a pulse frequency having a pulse period, said repeating temporal signals including a portion of the pulse period with including an auditory frequency of from 240 Hz to 480 Hz and a portion of the pulse period.

An example embodiment 60 including example embodiment 59, wherein said portion of said pulse period is one half of the pulse period.

An example embodiment 61 including any one of example embodiments 59 and 60, wherein said sequence of stimulus patterns includes a first stimulus pattern having a first pulse frequency, a second stimulus pattern having a second pulse frequency less than the first pulse frequency, and a third stimulus pattern having a third pulse frequency less than the second pulse frequency.

An example embodiment 62 including example embodiment 61, wherein the first pulse frequency is between 3.75 Hz and 4.25 Hz, the second pulse frequency is between 1.25 Hz and 1.75 Hz, and the third pulse frequency is between 0.25 Hz and 0.75 Hz.

An example embodiment 63 including example embodiment 62, wherein the first pulse frequency is 3.9 Hz, the second pulse frequency is 1.5 Hz, and the third pulse frequency is 1 Hz.

An example embodiment 64 including any one of example embodiments 61 through 63, wherein said first stimulus pattern, said second stimulus pattern, or said third stimulus pattern stimulates for a predetermined time interval.

An example embodiment 65 including example embodiment 64, wherein the predetermined time interval is 25-35 seconds.

An example embodiment 66 including example embodiment 64, wherein the predetermined time interval is 30 seconds.

An example embodiment 67 including any one of example embodiments 54 through 66, wherein the headset is in operative communication with an external control device.

An example embodiment 68 comprises a method of treating a neurological disease or condition or providing performance enhancement using the method of example embodiment 54.

An example embodiment 69 including example embodiment 68, where said neurological disease or condition comprises insomnia, post-traumatic stress disorder (PTSD), or brain injuries such as traumatic brain injury (TBI), mild traumatic brain injury (mTBI), or strokes.

An example embodiment 70 including example embodiment 68, where said performance enhancement is providing sleep, the improvement of mental capabilities, or the improvement of physical capabilities.

Figure 5:
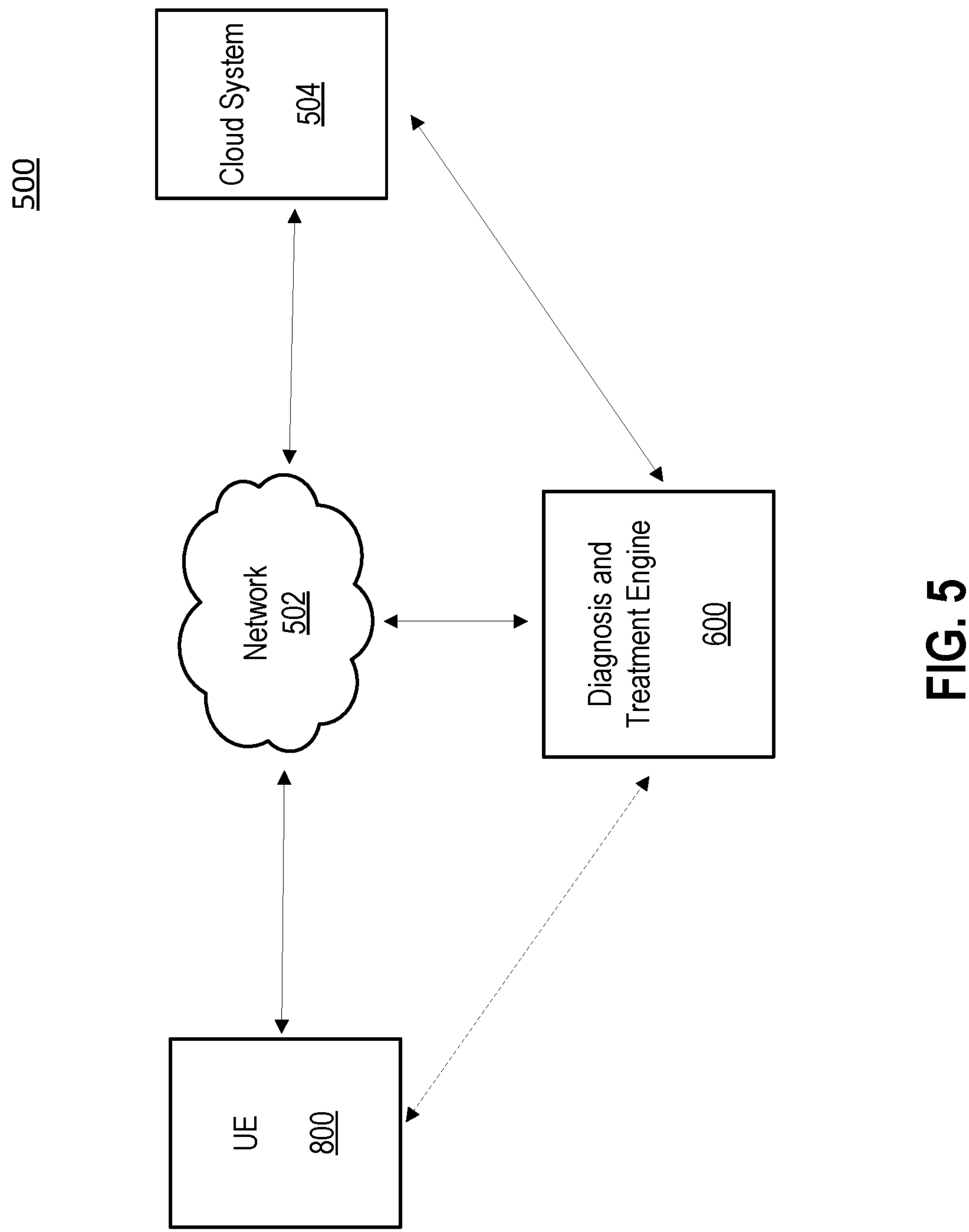
FIG. 5 is a block diagram of an example configuration within which the systems and methods disclosed herein could be implemented according to some embodiments of the present disclosure.

With reference to FIG. 5, system (or framework) 500 is depicted which includes UE 800 (e.g., a client device), network 502, cloud system 504 and diagnosis and treatment engine 600.

Figure 8:
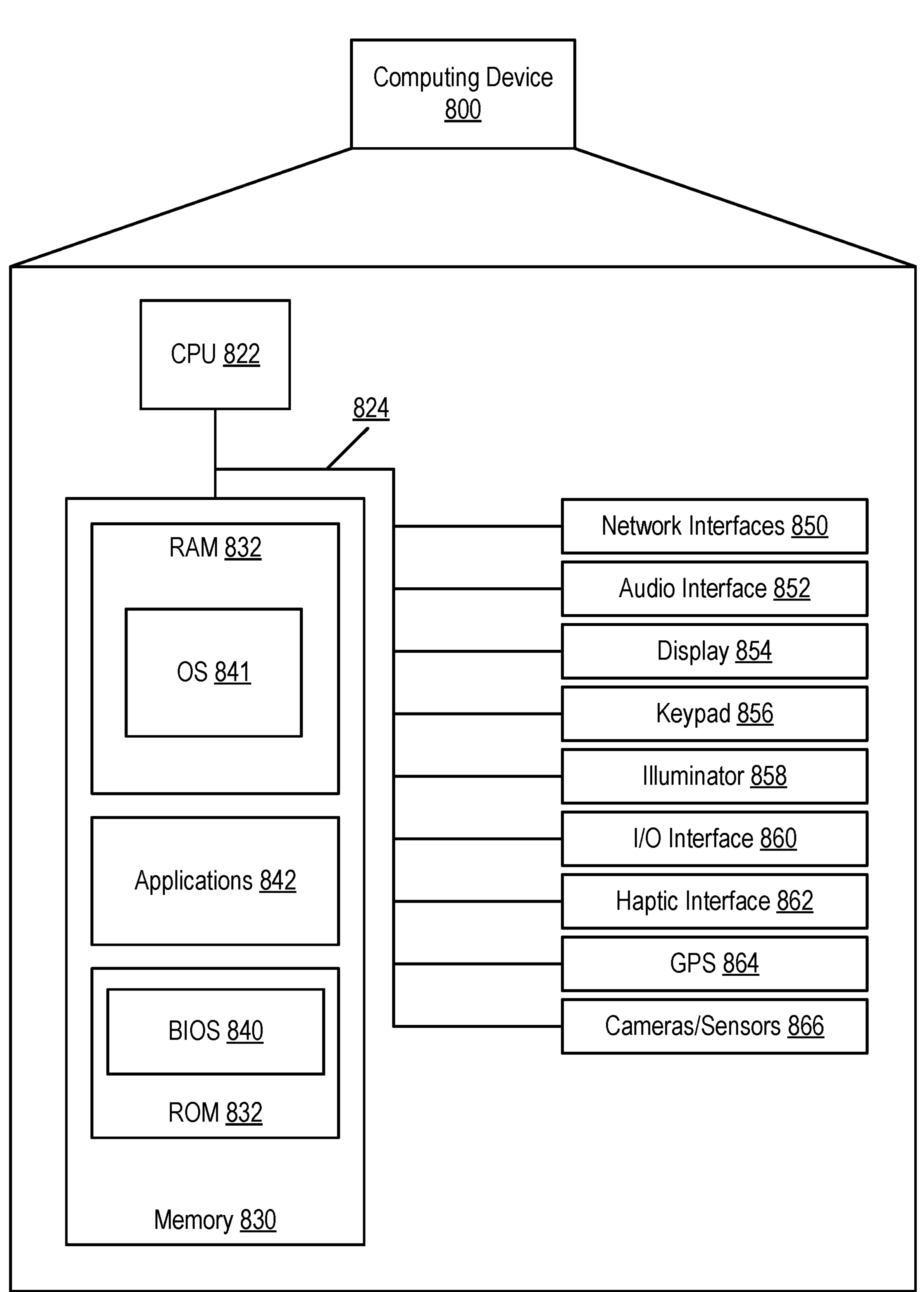
FIG. 8 is a block diagram illustrating a computing device showing an example of a device used in various embodiments of the present disclosure.

As discussed above, UE 800 can be can be part of the system or components discussed above in reference to FIGS. 1-4. In some embodiments, UE 800 can be any type of device, such as, but not limited to, a medical device, mobile phone, tablet, laptop, personal computer, sensor, Internet of Things (IoT) device, autonomous machine, and any other device equipped with a cellular or wireless or wired transceiver. An example of such is depicted in FIG. 8, discussed below.

In some embodiments, as discussed above at least in relation to FIGS. 1-4, UE 800 can be a medical device, or another device that is communicatively coupled to a medical device that enables reception of readings from sensors of the medical device. For example, in some embodiments, UE 800 can be a wearable neurostimulation device (e.g., system 100). In another example, in some embodiments, UE 800 can be a user's smartphone that is connected via WiFi, Bluetooth Low Energy (BLE) or NFC, for example, to a peripheral neurostimulation device. An example of this is depicted in FIG. 3A. Thus, in some embodiments, UE 800 can be configured to receive data from sensors associated with a medical device, as discussed in more detail below.

Network 502 can be any type of network, such as, but not limited to, a wireless network, cellular network, the Internet, and the like (as discussed above). As discussed herein, network 502 can facilitate connectivity of the components of system 500, as illustrated in FIG. 5.

Cloud system 504 can be any type of cloud operating platform and/or network based system upon which applications, operations, and/or other forms of network resources can be located. For example, system 5104 can correspond to a service provider, network provider and/or medical provider from where services and/or applications can be accessed, sourced or executed from. In some embodiments, cloud system 504 can include a server(s) and/or a database of information which is accessible over network 502. In some embodiments, a database (not shown) of system 504 can store a dataset of data and metadata associated with local and/or network information related to a user(s) of UE 800, patients and the UE 800, and the services and applications provided by cloud system 504 and/or diagnosis and treatment engine 600.

Diagnosis and treatment engine 600, as discussed below in more detail, includes components for determining diagnostics and treatment plans for a patient, and facilitating execution of such treatment plans. That is, for example, engine 600 can enable UE 800 to detect, receive or otherwise identify electronic data related to a patient, determine conditions therefrom by which a medical disorder can be determined, and then, dynamically execute a treatment plan in a manner that accounts for characteristics of the patient and the iterative feedback received while treatments are being administered. Embodiments of how this is performed via engine 600, among others, are discussed in more detail below in relation to FIGS. 7A-7C.

According to some embodiments, diagnosis and treatment engine 600 can be a special purpose machine or processor and could be hosted by a device on network 502, within cloud system 504 and/or on UE 800. In some embodiments, engine 600 can be hosted by a peripheral device connected to UE 800 (e.g., a medical device, as discussed above in relation to FIGS. 1-4).

According to some embodiments, diagnosis and treatment engine 600 can function as an application provided by cloud system 504. In some embodiments, engine 600 can function as an application installed on UE 800. In some embodiments, such application can be a web-based application accessed by UE 800 over network 502 from cloud system 504 (e.g., as indicated by the connection between network 502 and engine 600, and/or the dashed line between UE 800 and engine 600 in FIG. 5). In some embodiments, engine 600 can be configured and/or installed as an augmenting script, program or application (e.g., a plug-in or extension) to another application or program provided by cloud system 504 and/or executing on UE 800.

Figure 6:
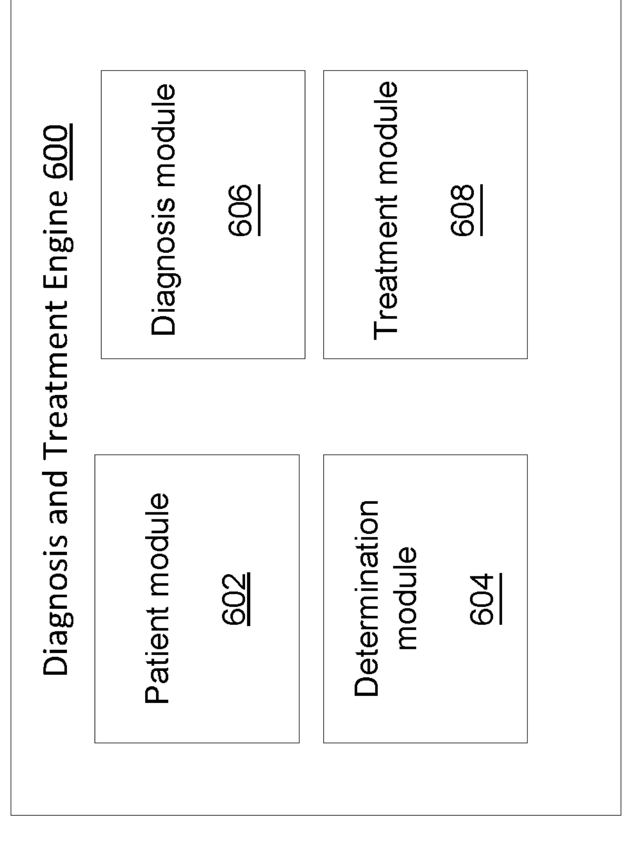
FIG. 6 is a block diagram illustrating components of an exemplary system according to some embodiments of the present disclosure.

As illustrated in FIG. 6, according to some embodiments, diagnosis and treatment engine 600 includes patient module 602, determination module 604, diagnosis module 606 and treatment module 608. It should be understood that the engine(s) and modules discussed herein are non-exhaustive, as additional or fewer engines and/or modules (or sub-modules) may be applicable to the embodiments of the systems and methods discussed. More detail of the operations, configurations and functionalities of engine 600 and each of its modules, and their role within embodiments of the present disclosure will be discussed below.

Figure 7A:
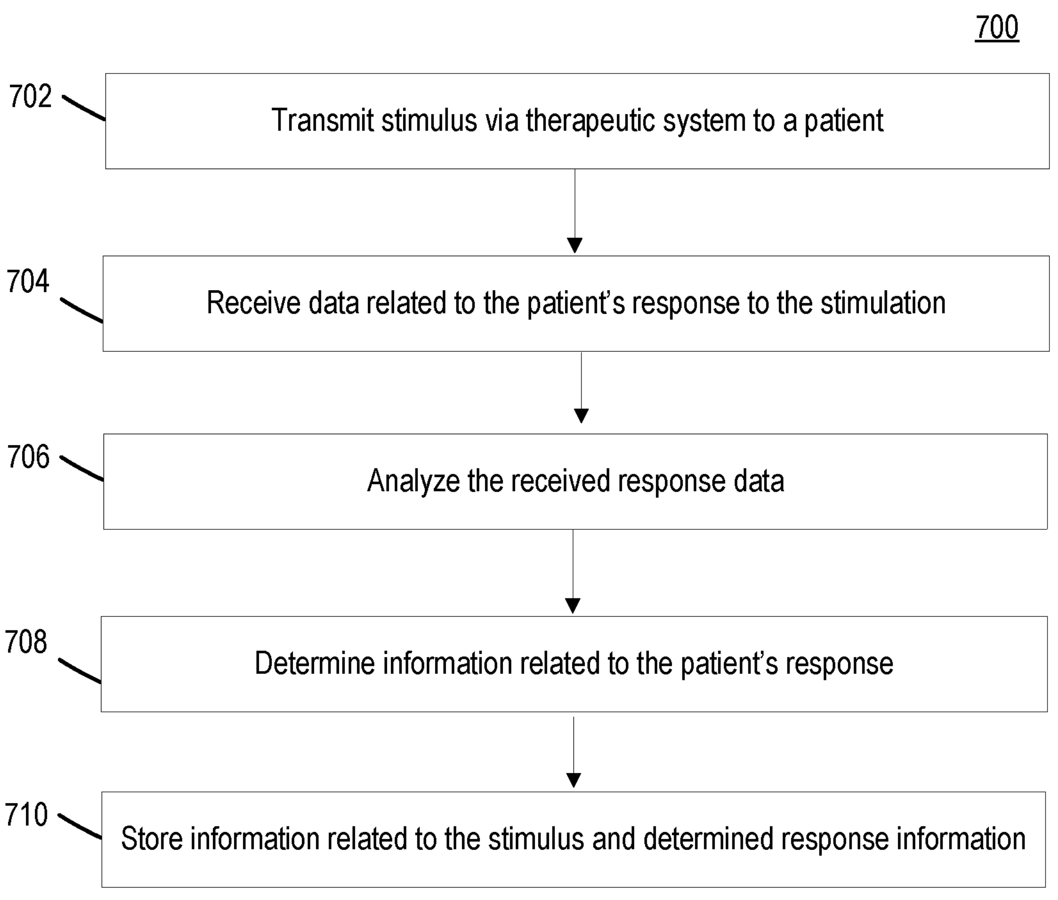
FIGS. 7A-7C illustrate exemplary data flows according to some embodiments of the present disclosure.
Figure 7B:
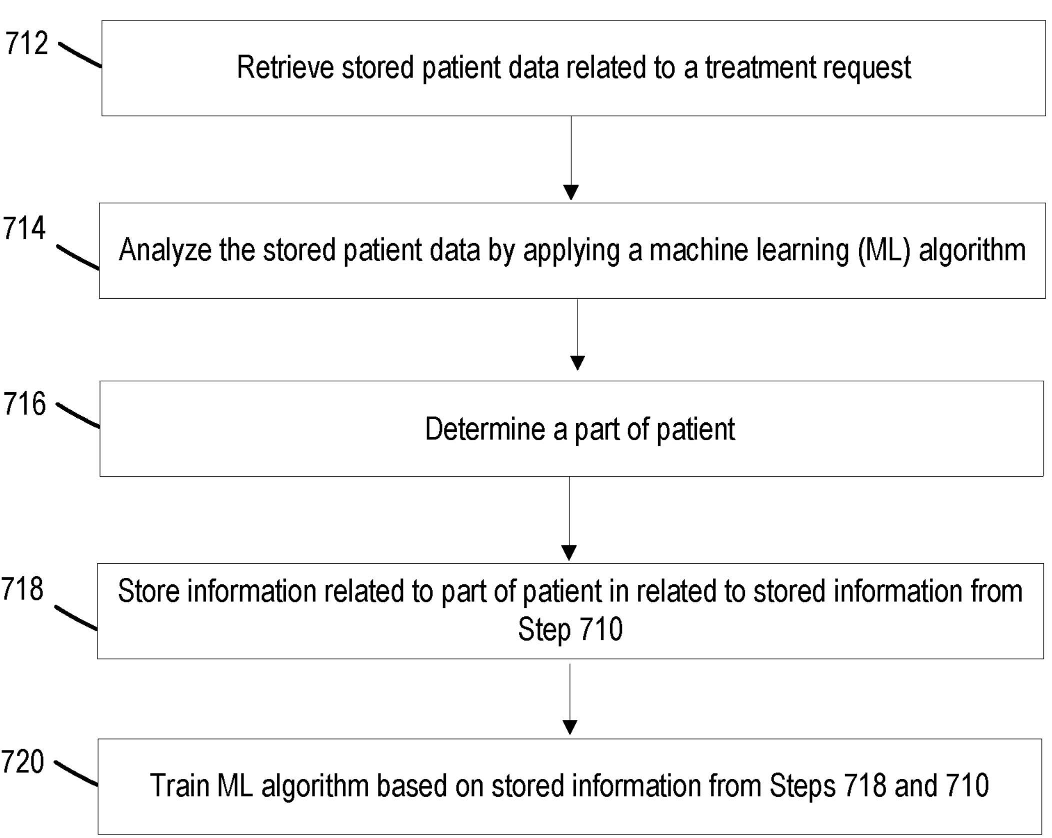
Figure 7C:
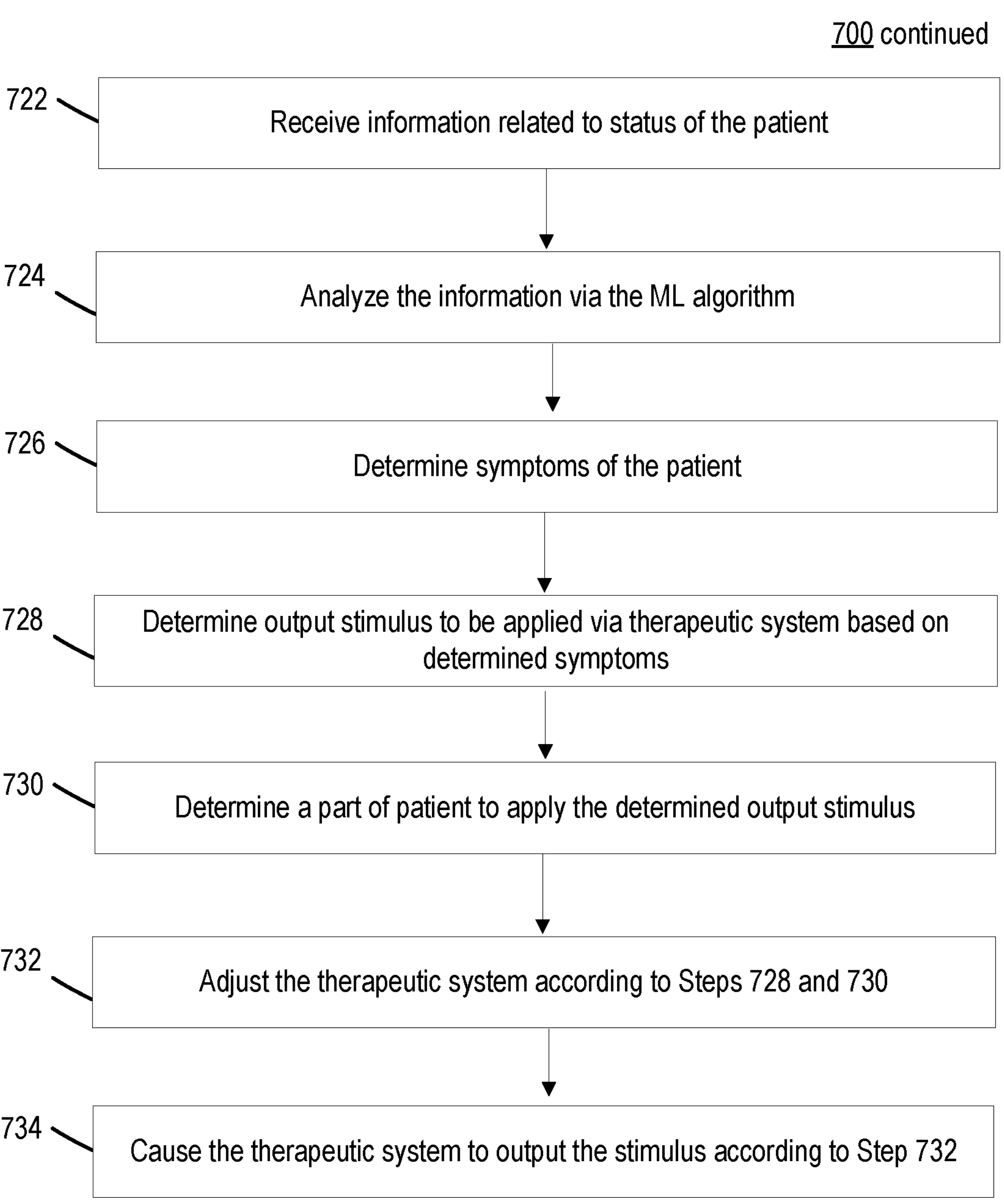

Turning now to FIGS. 7A-7C and Process 700, disclosed are embodiments for a computerized framework that detects medical conditions within patients, and dynamically effectuates a medical treatment involving electronic stimuli.

According to some embodiments, the disclosed framework is configured for analyzing data associated with a patient received from interactions with a patient's visual cortex, determining underlying conditions of the patient, then automatically causing medical equipment to output electronic stimuli that can address the medical condition(s) detected. As discussed herein, the disclosed framework can determine a correlation between a patient's attributes, electronic data of a condition of a patient and a medical disorder, and cause a device (e.g., a neurostimulation device of FIGS. 3A-3B, for example) to treat and monitor improvements of the condition and disorder. In some embodiments, the framework can be configured to focus on particular body parts of a patient (e.g., a part of the visual cortex) that has been identified as a part that is associated with particular symptoms and enables treatment, as well as a part that facilitates the most efficient treatment for a recovery.

It should be understood that while the disclosure herein will be discussed with reference to engine 600 executing a Machine Learning (ML) algorithm, technique, technology or mechanism, it should not be construed as limiting, as any type of trainable software, technology and/or executable computer/program-logic can be utilized in a similar manner without departing from the scope of the instant disclosure. For example, an algorithm can be any type of known or to be known, ML algorithm, artificial intelligence (AI) algorithm, greedy algorithm, recursive algorithm, and the like, or some combination thereof. Moreover, the ML algorithm can be any type of known or to be known support vector machine or logistic regression predictive modelling, and the like.

According to some embodiments, Process 700 will discussed in reference to stimulation of the visual cortex via electronic stimuli provided through/via a patient's eye. For example, as discussed above in reference to FIGS. 3A-3B above, visual stimuli can be provided by UE 800 (embodied as system 100 of FIGS. 3A and 3B, for example) where stimuli can be provided to particular visual cortex portions via the eye of a patient.

It should be noted that while discussion herein focuses on the visual cortex, it should not be construed as limiting, as electronic stimuli of other portions of the cerebral cortex (e.g., auditory cortex) via other body parts of a patient (e.g., ear, for example) would be understood by those of skill in the art to be included as alternative embodiments of the framework disclosed in the instant disclosure.

FIG. 7A discloses a portion of Process 700 that is related to engine 600 learning information related to portions of a patient response to types of electronic stimuli. For example, FIG. 7A involves the determination of how the patient's visual cortex responds to a type of electronic stimuli, which can include, but is not limited to a pattern, rate, shape, letter, frequency, quantity, volume, intensity, brightness, contrast, current, voltage, and the like, or some combination thereof. Accordingly, as discussed herein, electronic stimuli can correspond to electronic data that can be sent to a patient, viewed by a patient (e.g., visual cues) and output at specific values (e.g., different frequencies to impact/reach different parts/levels of the visual cortex or brain).

According to some embodiments, Steps 702-704 of Process 700 can be performed by patient module 602 of diagnosis and treatment engine 600; Steps 706-708 can be performed by determination module 604; and Step 710 can be performed by diagnosis module 606.

While the discussion herein related to Process 700 (for FIGS. 7A-7C) is being discussed in relation to an individual patient, it should be understood that the applicability of such processing can be extended to any number of patients (e.g., a small test group to a particular demographic, for example) without departing from the scope of the instant disclosure.

Process 700 begins with Step 702 where engine 600 causes the therapeutic system to transmit an electronic stimulus to the patient. For example, Step 702 can involve engine 600 causing an output of a visual stimuli via source 110L and/or 110R, which can be targeted to the patient's visual cortex via the patient's eye (or retina). For example, a set of vertical line patterns can be transmitted.

In Step 704, in response to the transmitted stimuli, engine 600 can receive data related to the patient's response to the stimulation. In some embodiments, this can involve receiving data related to how the targeted visual cortex (from Step 702) responded, which can include, but is not limited to, which portions of the visual cortex responded in particular manners, which portions of the stimulus caused certain types of responses, a quantity of a response, and other forms of biometric data, and the like.

According to some embodiments, Step 704 can involve the reception, retrieval, collection or otherwise identification of biometric data related to a patient that corresponds to how the patient responded to the transmitted stimuli. According to some embodiments, the types of biometric data can correspond to a type of transmitted stimuli, testing or monitored readings (or activity) that are being performed, and can also correspond to a type of medical device (and/or sensor) being used, and the like, or some combination thereof. In some embodiments, the biometric data can correspond to, but is not limited to, heart rate variability (HRV) data, EOG (electrooculography) data, Electroencephalography (EEG) data, eye tracking data, visual cortical data, and the like.

In Step 706, engine 600 can analyze the received data by performing a computational analysis of the data. According to some embodiments, the computational analysis performed in Step 706 can involve the received biometric data being used as an input to any type of ML/AI computational analysis algorithm, technology, mechanism or classifier, such as, but not limited to, neural networks (e.g., artificial neural network analysis (ANN), convolutional neural network (CNN) analysis, and the like), computer vision, cluster analysis, data mining, Bayesian network analysis, Hidden Markov models, logical model and/or tree analysis, and the like.

As a result of the analysis performed in Step 708, engine 600 can determine information related to the patient's visual cortex response. In some embodiments, Step 708 can involve the determination of what type of response the visual cortex had to each portion of the transmitted stimulation. In some embodiments, the determination can provide a mapping of particular scene-selective regions of the visual cortex, which can indicate how they responded to different types/categories of stimulations (or properties of the stimulation, such as, for example, orientation, spatial frequency, spatial location, shape, size, brightness, contrast, and the like).

Thus, Step 708 can enable engine 600 to determine, discern or otherwise identify how the patient's visual cortex responds to specific types of stimulation, which can indicate properties of the responses as well as which portions of the visual cortex perpetuated such response.

In Step 710, engine 600 can store information related to the data received, processed and determined in Steps 704-708. In some embodiments, an electronic medical record (EMR) for the patient can be created (and/or updated) and stored in a data store (of system 504) which can indicate the determined response as well as the data received that indicated such response. In some embodiments, information related to the transmitted stimulus can also be stored in the EMR which can provide insight as to how such a response was triggered.

According to some embodiments, this stored information can also be used to train the ML algorithm (of Step 706) being executed by engine 600.

Turning to FIG. 7B, Process 700 continues with Steps 712-720 which provide embodiments for leveraging the stored information (from Step 710) to treat a patient.

According to some embodiments, Step 712 of Process 700 can be performed by patient module 602 of diagnosis and treatment engine 600; Steps 714-716 can be performed by determination module 604; and Steps 718-720 can be performed by diagnosis module 606.

In Step 712, a request can be received to treat a patient, whereby engine 600 operates to retrieve the data stored (from Step 710). In some embodiments, the request can be automatically triggered by UE 800/system 100, by a health care professional, by a patient, and the like. The request can include information related to, but not limited to, a medical diagnosis, symptoms, a patient's EMR, a prescription or treatment plan (with an expected/requested result—for example an output pattern of electronic stimuli with determined characteristics of duration, frequency, time, current, and the like), and the like, or some combination thereof.

In Step 714, upon retrieving the stored patient data, engine 600 then operates to comparatively analyze the retrieved data based on the treatment request. According to some embodiments, Step 714 can involve parsing the stored data and request to determine which information is relevant for the treatment being requested. That is, for example, Step 714 can involve determining, deriving or otherwise identifying a type of treatment being requested, whereby engine 600 can then parse the retrieved patient data and mine for diagnostic data that corresponds to a type of treatment. Upon identifying this information, engine 600 can then perform a comparative analysis via a trained ML/AI algorithm. Accordingly, such ML/AI processing can be performed in a similar manner as discussed above at least in relation to Steps 706-708.

As a result of the processing of Step 714, engine 600 can perform Step 716 and determine a part of the patient to target with the requested treatment (from Step 712). That is, the analysis of Step 714 enables engine 600 to determine which portion of the eye and/or visual cortex to target with a requested treatment to produce a requested result.

By way of a non-limiting example, based on a request that a horizontal pattern of electronic stimuli for 3 minutes is to be input, engine 300 can determine that each input is to be provided via both sources 110L and 110R of system 100 (e.g., UE 800), and focused on the retina of each eye so as to trigger the parahippocampal place area (PPA) of the visual cortex.

In Step 718, the information related to the determination can be stored in a similar manner as discussed above (at least in relation to Step 710). Similarly, in Step 720, the information stored in Step 718, in connection with the stored data from Step 710, can be utilized to train the ML/AI algorithm, in a similar manner as discussed above.

Turning to FIG. 7C, Process 700 continues with Steps 722-734 which provide embodiments for applying or utilizing the stored information (from Steps 710 and 718) to treat a patient.

According to some embodiments, Step 722 of Process 700 can be performed by patient module 602 of diagnosis and treatment engine 600; Step 724-726 can be performed by determination module 604; Steps 728-730 can be performed by diagnosis module 606; and Steps 732-734 can be performed by treatment module 608.

In Step 722, information related to the status of the patient is received by engine 600. In some embodiments, the operation of Step 722 can be based on a request to treat a patient in a similar manner as discussed above in Step 712.

In some embodiments, such status information can be part of or based on a profile (or EMR) of the patent. Such profile can include any type of patient information, including, but not limited to, an identity (ID), name, address, age, race, gender (and/or any other type of demographic or geographic information), medical history, prescription history, family medical history, insurance information, collected biometric data, and the like, or some combination thereof.

In Step 724, engine 600 analyzes the status information of the patient, which can be performed in a similar manner as discussed above at least in relation to Step 706. As a result, engine 600 can perform Step 726 which involves determining symptoms of the patient related to a medical condition. That is, engine 600 can determine that, based on the status information received in Step 722, the patient suffers from a particularly determined condition. For example, based on current HRV data in patient' profile (e.g., low HRV data), the patient can be determined to have poor cognitive performance of visuospatial working memory (VSWM).

In Step 728, engine 600 can then determine a type and value of output stimuli to be applied via therapeutic system 100 (e.g., UE 800) based on the determined symptoms/conditions (from Step 726). For example, engine 600 can determine that a particular output pattern for a particular period of time is to be output to treat the detected symptoms/condition (e.g., an electronic output of X stimulus will improve the low HRV). Such determination can be performed via the ML/AI algorithms discussed above being applied to the output from Step 726.

In Step 730, engine 600 additionally determines which part of the patient to apply the determined output stimulus. In some embodiments, the determination can identify, but is not limited to, a quantity of eyes to receive stimulus (e.g., one or both eyes), the part of the eyes, dimensions and/or locations of the eyes (e.g., distance apart and other measurements of the patient's eyes, face and head), a part of the visual cortex, and the like, or some combination thereof. The determination of Step 730 can be performed via the ML/AI algorithms discussed above being applied to at least the output from Steps 726 and 728.

In Step 732, the therapeutic system is automatically adjusted (or configured) based on the determinations of Steps 728 and 730. For example, system 100 is adjusted to output X via source 110L and output Y via source 110R for a period of Z at a pattern/rate of ABC. Moreover, system 100 can be configured to focus the output on specific portions of the eye so as to trigger specific portions of the visual cortex (e.g., move or adjust positioning of the sources 110L and 110R to proper positions given the measurements of the patient's face and/or the therapeutic system 100). Thus, these adjustments can involve the physical manipulation of the system 100's components in order to prepare the system 100 to provide a treatment (of Step 712) according to the determinations of Steps 728 and 730.

In Step 734, engine 600 causes the therapeutic system to output the stimulus via the implementation of the adjusted system from Step 732. Thus, a requested treatment can be effectuated via focused electronic stimuli via a patient's eye(s) to a directed portion of their visual cortex.

In some embodiments, Process 734 can recursively proceed back to Step 704 so that medical records can be updated, and that the ML/AI algorithm operated by engine 600 can be further trained based on the execution of Step 734.

Thus, Process 700 provides a non-limiting example embodiment of implementing a trained ML algorithm embodied by engine 600 that can automatically execute a treatment plan for a medical condition by controlling a medical device to effectuate the most accurate and efficient manner for the treatment plan.

FIG. 8 is a block diagram illustrating a computing device 800 (e.g., UE 800, as discussed above) showing an example of a client device or server device used in the various embodiments of the disclosure.

The computing device 800 may include more or fewer components than those shown in FIG. 8, depending on the deployment or usage of the device 800. For example, a server computing device, such as a rack-mounted server, may not include audio interfaces 852, displays 854, keypads 856, illuminators 858, haptic interfaces 862, GPS receivers 864, or cameras/sensors 866. Some devices may include additional components not shown, such as graphics processing unit (GPU) devices, cryptographic co-processors, AI accelerators, or other peripheral devices.

As shown in FIG. 8, the device 800 includes a central processing unit (CPU) 822 in communication with a mass memory 830 via a bus 824. The computing device 800 also includes one or more network interfaces 850, an audio interface 852, a display 854, a keypad 856, an illuminator 858, an input/output interface 860, a haptic interface 862, an optional GPS receiver 864 (and/or an interchangeable or additional GNSS receiver) and a camera(s) or other optical, thermal, or electromagnetic sensors 866. Device 800 can include one camera/sensor 866 or a plurality of cameras/sensors 866. The positioning of the camera(s)/sensor(s) 866 on the device 800 can change per device 800 model, per device 800 capabilities, and the like, or some combination thereof.

In some embodiments, the CPU 822 may comprise a general-purpose CPU. The CPU 822 may comprise a single-core or multiple-core CPU. The CPU 822 may comprise a system-on-a-chip (SoC) or a similar embedded system. In some embodiments, a GPU may be used in place of, or in combination with, a CPU 822. Mass memory 830 may comprise a dynamic random-access memory (DRAM) device, a static random-access memory device (SRAM), or a Flash (e.g., NAND Flash) memory device. In some embodiments, mass memory 830 may comprise a combination of such memory types. In one embodiment, the bus 824 may comprise a Peripheral Component Interconnect Express (PCIe) bus. In some embodiments, the bus 824 may comprise multiple busses instead of a single bus.

Mass memory 830 illustrates another example of computer storage media for the storage of information such as computer-readable instructions, data structures, program modules, or other data. Mass memory 830 stores a basic input/output system ("BIOS") 840 for controlling the low-level operation of the computing device 800. The mass memory also stores an operating system 841 for controlling the operation of the computing device 800.

Applications 842 may include computer-executable instructions which, when executed by the computing device 800, perform any of the methods (or portions of the methods) described previously in the description of the preceding Figures. In some embodiments, the software or programs implementing the method embodiments can be read from a hard disk drive (not illustrated) and temporarily stored in RAM 832 by CPU 822. CPU 822 may then read the software or data from RAM 832, process them, and store them to RAM 832 again.

The computing device 800 may optionally communicate with a base station (not shown) or directly with another computing device. Network interface 850 is sometimes known as a transceiver, transceiving device, or network interface card (NIC).

The audio interface 852 produces and receives audio signals such as the sound of a human voice. For example, the audio interface 852 may be coupled to a speaker and microphone (not shown) to enable telecommunication with others or generate an audio acknowledgment for some action. Display 854 may be a liquid crystal display (LCD), gas plasma, light-emitting diode (LED), or any other type of display used with a computing device. Display 854 may also include a touch-sensitive screen arranged to receive input from an object such as a stylus or a digit from a human hand.

Keypad 856 may comprise any input device arranged to receive input from a user. Illuminator 858 may provide a status indication or provide light.

The computing device 800 also comprises an input/output interface 860 for communicating with external devices, using communication technologies, such as USB, infrared, Bluetooth™, or the like. The haptic interface 862 provides tactile feedback to a user of the client device.

The optional GPS transceiver 864 can determine the physical coordinates of the computing device 800 on the surface of the Earth, which typically outputs a location as latitude and longitude values. GPS transceiver 864 can also employ other geo-positioning mechanisms, including, but not limited to, triangulation, assisted GPS (AGPS), E-OTD, CI, SAI, ETA, BSS, or the like, to further determine the physical location of the computing device 800 on the surface of the Earth. In one embodiment, however, the computing device 800 may communicate through other components, provide other information that may be employed to determine a physical location of the device, including, for example, a MAC address, IP address, or the like.

For the purposes of this disclosure a module is a software, hardware, or firmware (or combinations thereof) system, process or functionality, or component thereof, that performs or facilitates the processes, features, and/or functions described herein (with or without human interaction or augmentation). A module can include sub-modules. Software components of a module may be stored on a computer readable medium for execution by a processor. Modules may be integral to one or more servers, or be loaded and executed by one or more servers. One or more modules may be grouped into an engine or an application.

For the purposes of this disclosure the term "user", "subscriber" "consumer" or "customer" should be understood to refer to a user of an application or applications as described herein and/or a consumer of data supplied by a data provider. By way of example, and not limitation, the term "user" or "subscriber" can refer to a person who receives data provided by the data or service provider over the Internet in a browser session, or can refer to an automated software application which receives the data and stores or processes the data.

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible.

Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure.

What is claimed is:

1. A method comprising the steps of:

receiving, by a device, a request to provide a medical treatment to a patient, the medical treatment comprising instructions related to electronic stimuli to be output via a therapeutic medical device and delivered to a visual cortex of the patient, the treatment instructions further comprising information identifying at least one eye component of the therapeutic medical device to output the electronic stimuli;

identifying, by the device, a status of the patient, the status of the patient corresponding to a medical condition of the patient;

determining, by the device, a type and value of the electronic stimuli based on the identified status of the patient;

automatically causing, by the device, the therapeutic medical device to adjust a positioning of the at least one eye component based on the identified status and the determined type and value of the electronic stimuli, the adjusted positioning enabling the electronic stimuli to be output via the at least one eye component according to the type and value, the adjusted positioning further enabling the electronic stimuli to be directed to a particular body part of the patient; and causing the adjusted therapeutic medical device, by the device, to output the electronic stimuli provided in the medical treatment.

2. The method of claim 1, further comprising:

determining, by the device, based on the status of the patient and the determined type and value of the electronic stimuli, the particular body part of the patient, wherein the determination of the particular body part is based on the device executing a machine learning (ML) algorithm with the status of the patient and the determined type and value of the electronic stimuli as the input.

3. The method of claim 2, wherein the particular body part of the patient is at least one of a sub-part of at least one eye of the patient and a sub-part of the visual cortex of the patient.

4. The method of claim 3, wherein the particular body part of the patient corresponds to at least one of a quantity of eyes and dimensions and/or locations of the eyes.

5. The method of claim 1, further comprising:

identifying, by the device, a profile of the patient, the profile being an electronic medical record (EMR), the profile comprising information related to the status of the patient; and analyzing, by the device, the profile, and determining symptoms of the medical condition of the patient.

6. The method of claim 5, wherein the identified status of the patient corresponds to the determined symptoms of the medical condition.

7. The method of claim 5, wherein the profile comprises information related to at least one of an identity (ID), name, address, age, race, gender, demographic information, geographic information, medical history, prescription history, family medical history, insurance information and collected biometric data of the patient.

8. The method of claim 1, wherein the determination of the type and value of the electronic stimuli is based on the device executing a machine learning (ML) algorithm with the status as the input.

9. The method of claim 1, further comprising:

receiving, by the device, response data from a targeted portion of the visual cortex of the patient, the response data produced in response to the output of the electronic stimuli;

analyzing, by the device, the response data, and determining information related to the response of the patient; and storing, by the device, the response data and the determined information in an electronic medical record (EMR) of the patient, wherein the steps of the method are performed by the device executing a machine learning (ML) algorithm trained on the stored response data and determined information for a plurality of patients.

10. The method of claim 1, wherein the electronic stimuli is output according to at least one of a pattern, rate, shape, letter, frequency, quantity, volume, intensity, brightness, contrast, current and voltage.

11. The method of claim 1, wherein the therapeutic medical device is communicatively coupled to the device.

12. The method of claim 1, wherein the device is the therapeutic medical device.

13. A non-transitory computer-readable storage medium tangibly encoded with computer-executable instructions, that when executed by a device, perform a method comprising steps of:

receiving, by the device, a request to provide a medical treatment to a patient, the medical treatment comprising instructions related to electronic stimuli to be output via a therapeutic medical device and delivered to a visual cortex of the patient, the treatment instructions further comprising information identifying at least one eye component of the therapeutic medical device to output the electronic stimuli;

identifying, by the device, a status of the patient, the status of the patient corresponding to a medical condition of the patient;

determining, by the device, a type and value of the electronic stimuli based on the identified status of the patient;

automatically causing, by the device, the therapeutic medical device to adjust a positioning of the at least one eye component based on the identified status and the determined type and value of the electronic stimuli, the adjusted positioning enabling the electronic stimuli to be output via the at least one eye component according to the type and value, the adjusted positioning further enabling the electronic stimuli to be directed to a particular body part of the patient; and causing the adjusted therapeutic medical device, by the device, to output the electronic stimuli provided in the medical treatment.

14. The non-transitory computer-readable storage medium of claim 13, further comprising:

determining, by the device, based on the status of the patient and the determined type and value of the electronic stimuli, the particular body part of the patient, wherein the determination of the particular body part is based on the device executing a machine learning (ML) algorithm with the status of the patient and the determined type and value of the electronic stimuli as the input.

15. The non-transitory computer-readable storage medium of claim 14, wherein the particular body part of the patient is at least one of a sub-part of at least one eye of the patient and a sub-part of the visual cortex of the patient.

16. The non-transitory computer-readable storage medium of claim 15, wherein the particular body part of the patient corresponds to at least one of a quantity of eyes and dimensions and/or locations of the eyes.

17. The non-transitory computer-readable storage medium of claim 13, further comprising:

identifying, by the device, a profile of the patient, the profile being an electronic medical record (EMR), the profile comprising information related to the status of the patient; and analyzing, by the device, the profile, and determining symptoms of the medical condition of the patient, wherein the identified status of the patient corresponds to the determined symptoms of the medical condition.

18. The non-transitory computer-readable storage medium of claim 13, further comprising:

receiving, by the device, response data from a targeted portion of the visual cortex of the patient, the response data produced in response to the output of the electronic stimuli;

analyzing, by the device, the response data, and determining information related to the response of the patient; and storing, by the device, the response data and the determined information in an electronic medical record (EMR) of the patient.

19. A device comprising:

a processor configured to:

receive a request to provide a medical treatment to a patient, the medical treatment comprising instructions related to electronic stimuli to be output via a therapeutic medical device and delivered to a visual cortex of the patient, the treatment instructions further comprising information identifying at least one eye component of the therapeutic medical device to output the electronic stimuli;

identify a status of the patient, the status of the patient corresponding to a medical condition of the patient;

determine a type and value of the electronic stimuli based on the identified status of the patient;

automatically cause the therapeutic medical device to adjust a positioning of the at least one eye component based on the identified status and the determined type and value of the electronic stimuli, the adjusted positioning enabling the electronic stimuli to be output via the at least one eye component according to the type and value, the adjusted positioning further enabling the electronic stimuli to be directed to a particular body part of the patient; and cause the adjusted therapeutic medical device to output the electronic stimuli provided in the medical treatment.

20. The device of claim 19, wherein the processor is further configured to:

determine, based on the status of the patient and the determined type and value of the electronic stimuli, the particular body part of the patient, wherein the determination of the particular body part is based on the device executing a machine learning (ML) algorithm with the status of the patient and the determined type and value of the electronic stimuli as the input.

* * * * *